United States Patent
MacDonald et al.

(10) Patent No.: US 8,148,353 B2
(45) Date of Patent: Apr. 3, 2012

(54) POLYMORPHS OF FLUTICASONE FUROATE AND PROCESS FOR PREPARATION THEREOF

(75) Inventors: Peter Lindsay MacDonald, Gentilino (CH); Pierluigi Rossetto, Lodi (IT); Adrienne Kovacsne-Mezei, Debrecen (HU); Roman Gabriel, Olomoue (CZ); Alexandr Jegorov, Dobrá Voda (CZ); Jiri Faustmann, Opava-6 (CZ)

(73) Assignee: Plus Chemicals SA, Paradiso (CH)

( * ) Notice: Subject to any disclaimer, the term of this patent is extended or adjusted under 35 U.S.C. 154(b) by 349 days.

(21) Appl. No.: 12/462,782

(22) Filed: Aug. 6, 2009

(65) Prior Publication Data

US 2010/0130458 A1    May 27, 2010

Related U.S. Application Data

(60) Provisional application No. 61/188,394, filed on Aug. 7, 2008, provisional application No. 61/088,867, filed on Aug. 14, 2008, provisional application No. 61/107,925, filed on Oct. 23, 2008, provisional application No. 61/161,609, filed on Mar. 19, 2009, provisional application No. 61/169,977, filed on Apr. 16, 2009, provisional application No. 61/172,073, filed on Apr. 23, 2009.

(51) Int. Cl.
*A61K 31/58* (2006.01)
*C07J 11/00* (2006.01)

(52) U.S. Cl. .................. 514/172; 552/610
(58) Field of Classification Search .......... 514/172; 552/610

See application file for complete search history.

(56) References Cited

U.S. PATENT DOCUMENTS

| | | |
|---|---|---|
| 6,777,399 B2 | 8/2004 | Biggadike et al. |
| 6,777,400 B2 | 8/2004 | Biggadike et al. |
| 6,858,593 B2 | 2/2005 | Biggadike et al. |
| 7,101,866 B2 | 9/2006 | Biggadike et al. |

FOREIGN PATENT DOCUMENTS

| | | |
|---|---|---|
| WO | WO-02/12265 A1 | 2/2002 |
| WO | WO-02/12266 A1 | 2/2002 |
| WO | WO-03/066026 A1 | 8/2003 |
| WO | WO-03/066655 A1 | 8/2003 |
| WO | WO-2006/108572 A2 | 10/2006 |

*Primary Examiner* — Brandon Fetterolf
*Assistant Examiner* — Paul Zarek
(74) *Attorney, Agent, or Firm* — Kenyon & Kenyon LLP

(57) ABSTRACT

Provided are polymorphs of fluticasone furoate and processes for preparation thereof.

14 Claims, 26 Drawing Sheets

A PXRD pattern of Fluticasone furoate Form 4

POLYMORPHS OF FLUTICASONE FUROATE AND PROCESS FOR PREPARATION THEREOF

CROSS REFERENCE

The present invention claims the benefit of the following U.S. Provisional Patent Application Nos. 61/188,394 filed Aug. 7, 2008; 61/088,867 filed Aug. 14, 2008; 61/107,925 filed Oct. 23, 2008; 61/161,609 filed Mar. 19, 2009; 61/169,977 filed Apr. 16, 2009; and 61/172,073 filed Apr. 23, 2009. The contents of these applications are incorporated herein by reference.

FIELD OF THE INVENTION

The present invention relates to polymorphs of Fluticasone furoate, process for preparing said polymorphs, and pharmaceutical compositions thereof.

BACKGROUND OF THE INVENTION

Fluticasone furoate, S-(fluoromethyl) (6S,8S,9R,10S,11S,13S,14S,16R,17R)-6,9-difluoro-11,17-dihydroxy-10,13,16-trimethyl-3-oxo-6,7,8,11,12,14,15,16-octahydrocyclopenta[a]phenanthrene-17-carbothioate, has the following structure:

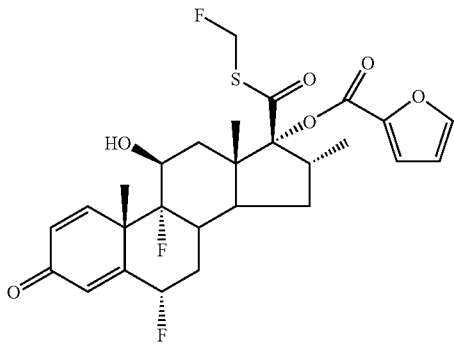

Fluticasone is a synthetic corticosteroid used for the treatment of asthma, allergic rhinitis. It can also be used in combination with salmeterol. It can also be used in a cream or ointment for the treatment of eczema and psoriasis Solvates of Fluticasone furoate are described in U.S. Pat. No. 7,101,866, U.S. Pat. No. 6,777,399, U.S. Pat. No. 6,777,400 and U.S. Pat. No. 6,858,593, incorporated herein by reference.

The present invention discloses new solid states forms of Fluticasone furoate.

Polymorphism, the occurrence of different crystal forms, is a property of some molecules and molecular complexes. A single molecule, like Fluticasone furoate, may give rise to a variety of crystalline forms having distinct crystal structures and physical properties like melting point, x-ray diffraction pattern, infrared absorption fingerprint, and solid state NMR spectrum. One crystalline form may give rise to thermal behavior different from that of another crystalline form. Thermal behavior can be measured in the laboratory by such techniques as capillary melting point, thermogravimetric analysis ("TGA"), and differential scanning calorimetry ("DSC") as well as content of solvent in the crystalline form, which have been used to distinguish polymorphic forms.

The difference in the physical properties of different crystalline forms results from the orientation and intermolecular interactions of adjacent molecules or complexes in the bulk solid. Accordingly, polymorphs are distinct solids sharing the same molecular formula yet having distinct advantageous physical properties compared to other crystalline forms of the same compound or complex.

One of the most important physical properties of pharmaceutical compounds is their solubility in aqueous solution, particularly their solubility in the gastric juices of a patient. For example, where absorption through the gastrointestinal tract is slow, it is often desirable for a drug that is unstable to conditions in the patient's stomach or intestine to dissolve slowly so that it does not accumulate in a deleterious environment. Different crystalline forms or polymorphs of the same pharmaceutical compounds can and reportedly do have different aqueous solubilities.

The discovery of new polymorphic forms and solvates of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. Therefore, there is a need for additional solid state forms of Fluticasone furoate.

SUMMARY OF THE INVENTION

In one embodiment, the present invention encompasses crystalline Fluticasone furoate characterized by data selected from a group consisting of: powder XRD pattern having peaks at about 8.7, 13.1, 13.3, 16.9 and 18.8±0.2 degrees two-theta; a PXRD pattern depicted in FIG. 1; and any combination thereof.

In another embodiment the present invention encompasses polymorphic pure crystalline Fluticasone furoate characterized by data selected from a group consisting of: powder XRD pattern having peaks at about 15.5, 16.6 and 18.8±0.2 degrees 2-theta and any 2 peaks selected from a list consisting of: 9.5, 10.9, 17.3, 17.8, 19.1, 19.7 and 21.8±0.2 degrees 2-theta; a PXRD pattern depicted in FIG. 3; a powder XRD pattern having peaks at about 15.5, 16.6, 18.8, 19.1 and 21.8±0.2 degrees 2 theta; a PXRD pattern depicted in FIG. 4; and any combination thereof.

In yet another embodiment, the present invention encompasses crystalline Fluticasone furoate characterized by data selected from a group consisting of: powder XRD pattern having peaks at about 9.0, 10.6, and 14.3±0.2 degrees two-theta, and any 2 peaks selected from a list consisting of: 14.8, 15.9, 17.8, 18.1, 18.6, 18.8 and 21.2±0.2 degrees 2-theta; a powder XRD pattern having peaks at about 9.0, 10.6, 14.3, 14.8 and 15.9±0.2 degrees two-theta; a PXRD pattern depicted in FIG. 7 and any combination thereof.

In one embodiment, the present invention encompasses crystalline Fluticasone furoate characterized by data selected from a group consisting of: powder XRD pattern having peaks at about 7.4, 12.5, and 17.7±0.2 degrees two-theta, and any 2 peaks selected from a list consisting of: 13.2, 15.3, 18.7, 19.6, 22.3 and 24.0±0.2 degrees 2-theta; a powder XRD pattern having peaks at about 7.4, 12.5, 15.3, 17.7 and 19.6±0.2 degrees two-theta; a PXRD pattern depicted in FIG. 9; a PXRD pattern depicted in FIG. 10; and any combination thereof.

In another embodiment, the present invention encompasses crystalline Fluticasone furoate characterized by data selected from a group consisting of: powder XRD pattern having peaks at about 8.6, 13.4, and 22.6±0.2 degrees two-theta, and any 2 peaks selected from a list consisting of: 10.8, 12.7, 14.5, 15.1, 19.0, 21.0 and 23.8±0.2 degrees 2-theta; a powder XRD pattern having peaks at about 8.6, 13.4, 15.1, 19.0 and 22.6±0.2 degrees two-theta; a PXRD pattern depicted in FIG. 12, and any combination thereof.

In yet another embodiment, the present invention encompasses crystalline Fluticasone furoate characterized by data selected from a group consisting of: powder XRD pattern having peaks at about 8.1, 9.6, 13.7, 14.6 and 15.2±0.2 degrees two-theta; a PXRD pattern depicted in FIG. 14, and any combination thereof.

In one embodiment, the present invention encompasses crystalline Fluticasone furoate characterized by data selected from a group consisting of: powder XRD pattern having peaks at about 9.9, 14.1, 15.1, 15.7 and 19.8±0.2 degrees two-theta; a PXRD pattern depicted in FIG. 16; and any combination thereof.

In another embodiment, the present invention encompasses crystalline Fluticasone furoate characterized by data selected from a group consisting of powder XRD pattern having peaks at about 12.1, 13.6, 15.1, 17.1 and 20.4±0.2 degrees two-theta; a PXRD pattern depicted in FIG. 18; and any combination thereof.

In yet another embodiment, the present invention encompasses solvates of Fluticasone furoate selected from a group consisting of: tert-Butanol, 2-butanol, dioxalane, 1,3 Dimethyl-3,4,5,6-tetrahydro-2(1H)-pyrimidinone ("DMPU") and, 3 dimethylimidazolidinone ("DMI")

The present invention further encompasses 1) a pharmaceutical composition comprising any one, or combination, of crystalline Forms of Fluticasone furoate described above and at least one pharmaceutically acceptable excipient and 2) the use of any one, or combination, of the above-described crystalline Forms of Fluticasone furoate, in the manufacture of a pharmaceutical composition, preferably wherein the pharmaceutical composition can be useful for the treatment of asthma, allergic rhinitis, eczema and psoriasis.

The pharmaceutical composition of the present invention can be in a solid or a non-solid form. If the pharmaceutical composition is in a non-solid form, any one, or combination of the crystalline Forms of Fluticasone furoate, within the composition, are retained as solid(s) in the non-solid pharmaceutical composition, e.g., as a suspension, foam, ointment etc.

The pharmaceutical composition can be prepared by a process comprising combining any one, or combination, of the above-described crystalline Forms of Fluticasone furoate with at least one pharmaceutically acceptable excipient. The crystalline Forms of Fluticasone furoate can be obtained by any of the processes of the present invention as described above.

The pharmaceutical composition can be used to make appropriate dosage forms such as tablets, powders, capsules, suppositories, sachets, troches and lozenges.

Any one, or combination, of the above-described crystalline Forms of Fluticasone furoate of the present invention, particularly in a pharmaceutical composition and dosage form, can be used to treat asthma, allergic rhinitis, eczema and psoriasis in a mammal such as a human, comprising administering a treatment effective amount of the one, or combination, of the crystalline Forms of Fluticasone furoate in the mammal. The treatment effective amount or proper dosage to be used can be determined by one of ordinary skill in the art, which can depend on the method of administration, the bioavailability, the age, sex, symptoms and health condition of the patient, and the severity of the disease to be treated, etc.

DETAILED DESCRIPTION OF THE INVENTION

The present invention relates to new solvates of Fluticasone furoate, process for preparing said solvates, and pharmaceutical compositions thereof.

As used herein, the term "room temperature" refers to a temperature between about 20° C. and about 30° C., preferably about 20° C. to about 25° C.

Figure 1:
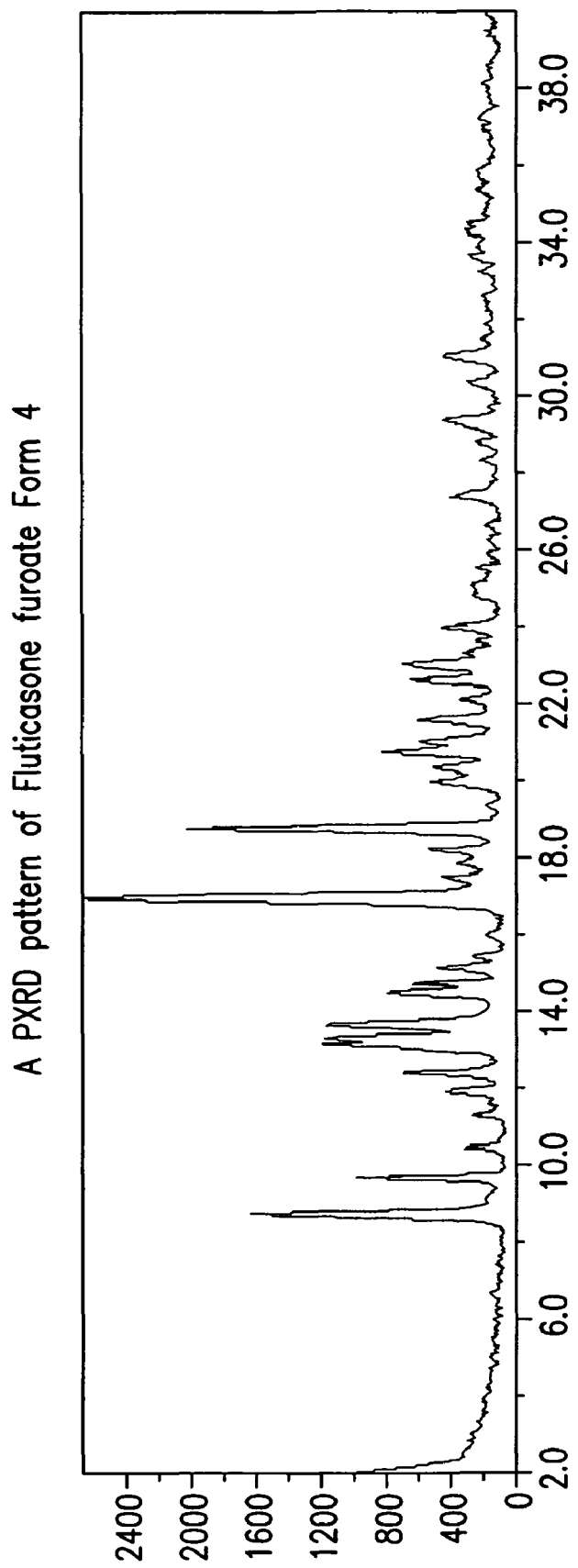
FIG. 1 illustrates a powder X-ray diffraction pattern of crystalline Fluticasone furoate designated form 4.

In one embodiment, the present invention encompasses a crystalline form of Fluticasone furoate characterized by data selected from a group consisting of: powder XRD pattern having peaks at about 8.7, 13.1, 13.3, 16.9 and 18.8±0.2 degrees two-theta; a PXRD pattern depicted in FIG. 1; and combination thereof. This crystalline form of Fluticasone furoate can be designated form 4.

Figure 2:
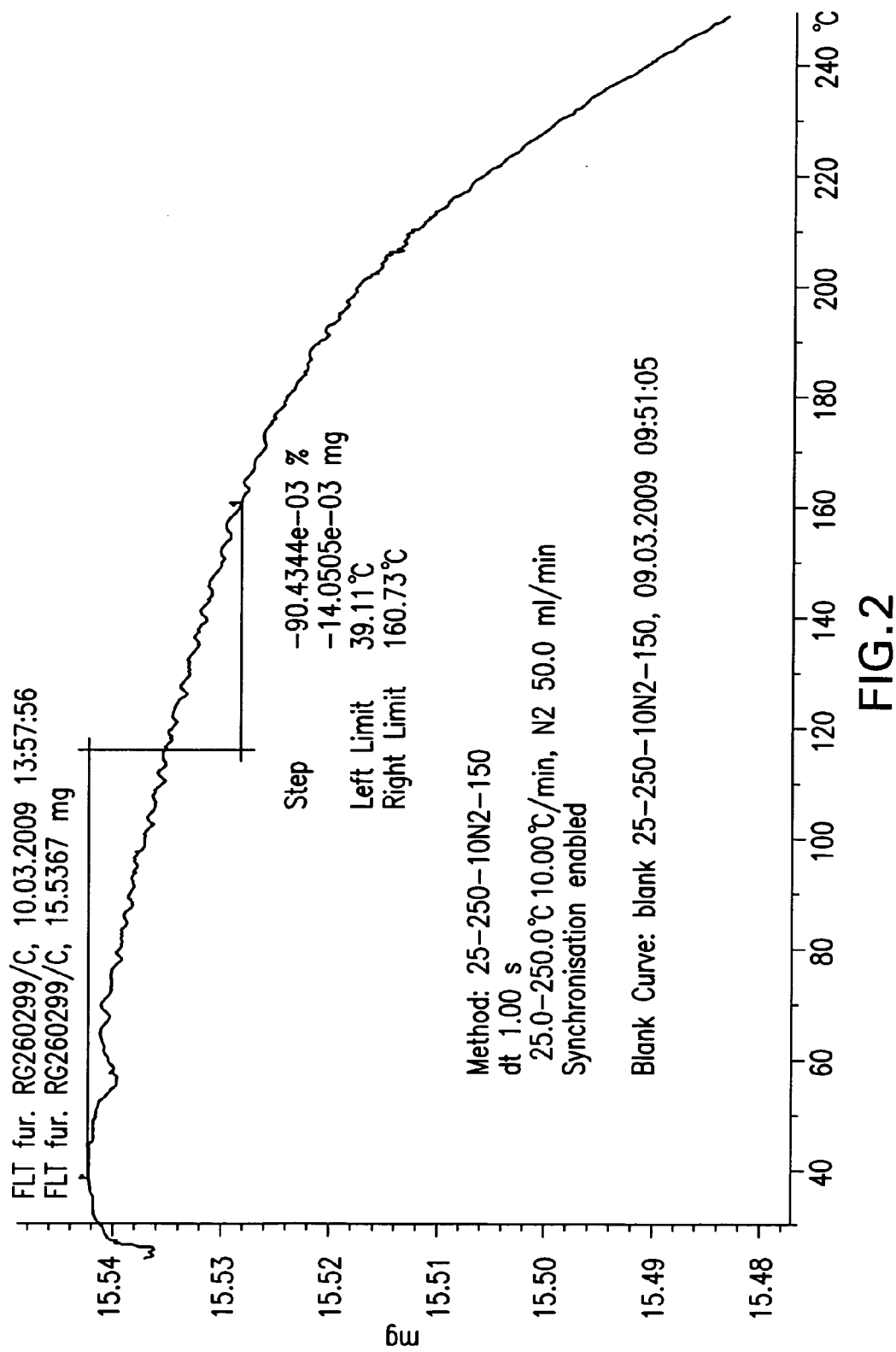
FIG. 2 illustrates a TGA pattern of crystalline Fluticasone furoate designated form 4.

The above form 4 of Fluticasone furoate can be further characterized by data selected from a group consisting of: a powder XRD pattern having peaks at about 9.6, 12.4, 14.5, 14.7 and 21.6±0.2 degrees 2-theta; a weight loss of up to about 0.3% at a temperature range of 25° C. to 160° C. as measured by TGA, a TGA pattern as depicted in FIG. 2; and any combination thereof.

Preferably, Fluticasone furoate form 4 is an anhydrous form of Fluticasone furoate.

As used herein, the term "anhydrous" in relation to crystalline Fluticasone furoate form 4 refers to a crystalline Fluticasone furoate which contains not more than 1% (w/w) of either water or organic solvents as measured by TGA.

The above form 4 can be prepared by a process comprising suspending Dimethylacetamide ("DMAc") solvate of Fluticasone furoate in a solvent selected form a group consisting of: 1-pentanol, isobutylacetate, methylal, ethylal and propylal; cooling the suspension to obtain a second suspension; and heating the second suspension.

The starting Fluticasone furoate Dimethylacetamide ("DMAc") solvate can be prepared, for example, according to the process of U.S. Pat. No. 6,777,399 examples 15.

The suspension can be provided by combining DMAc solvate of Fluticasone furoate and the solvent.

The suspension is cooled to obtain a second suspension. Preferably, cooling is to a temperature of about 0° C., preferably, over a period of about 10 minutes.

Preferably, the second suspension is further maintained after cooling, preferably upon stirring. Preferably, maintaining is done at a temperature of about 0° C., preferably for a period of about 10 minutes.

The second suspension is heated, preferably, to a temperature of about 42° C. to about 98° C., depending on the solvent. For example, when 1-pentanol is used, the suspension is heated to a temperature of about 80° C., when isobutylacetate is used the suspension is heated to a temperature of about 98° C.; when methylal is used the suspension is heated to a temperature of about 42° C.; when ethylal is used it is heated to a temperature of about 86° C.; and when propylal is used the suspension is heated to a temperature of about 80° C.

Preferably, heating is done over a period of about 1 hour.

After heating, the second suspension can be further maintained at the same temperature, preferably it is maintained upon stirring. Preferably, maintaining is for a period of about 10 minutes.

Further, the second suspension is cooled.

Typically, cooling is performed prior to performing a recovery process.

Preferably, cooling is to a temperature of about 0° C., preferably over a period of about 1 hour.

The second suspension can then be further maintained. Preferably, maintaining is done upon stirring, preferably for a period of about 2 hours.

The process for preparing crystalline form 4 may further comprise recovering the said crystalline form The recovery process may comprise, for example, filtering the said crystalline form and drying. Preferably drying is done under nitrogen. Preferably, drying is done at a temperature of about 35° C., preferably for a period of about 60 minutes.

Figure 3:
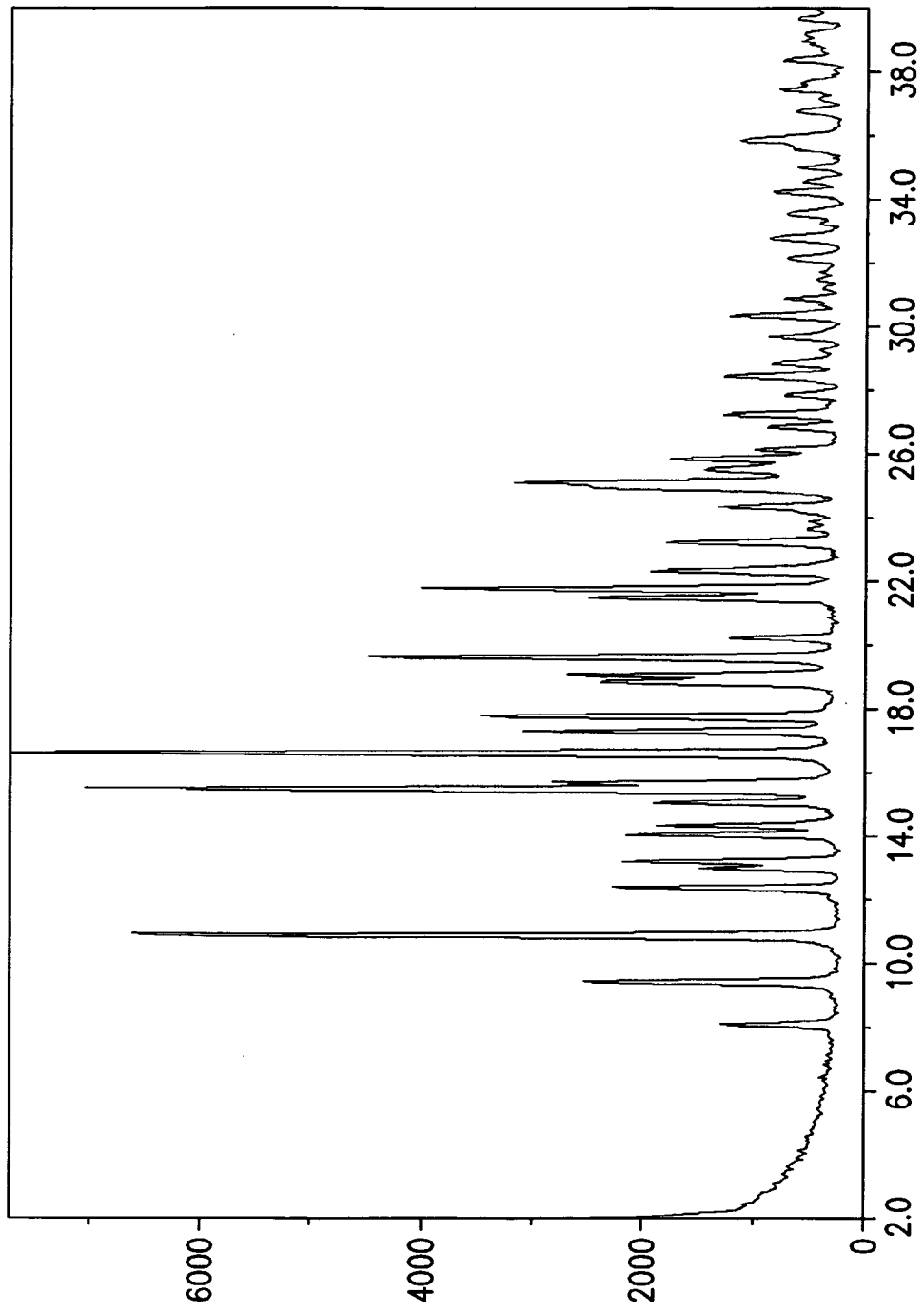
FIG. 3 illustrates a powder X-ray diffraction pattern of polymorphic pure crystalline Fluticasone furoate designated form A obtained in example 6.
Figure 4:
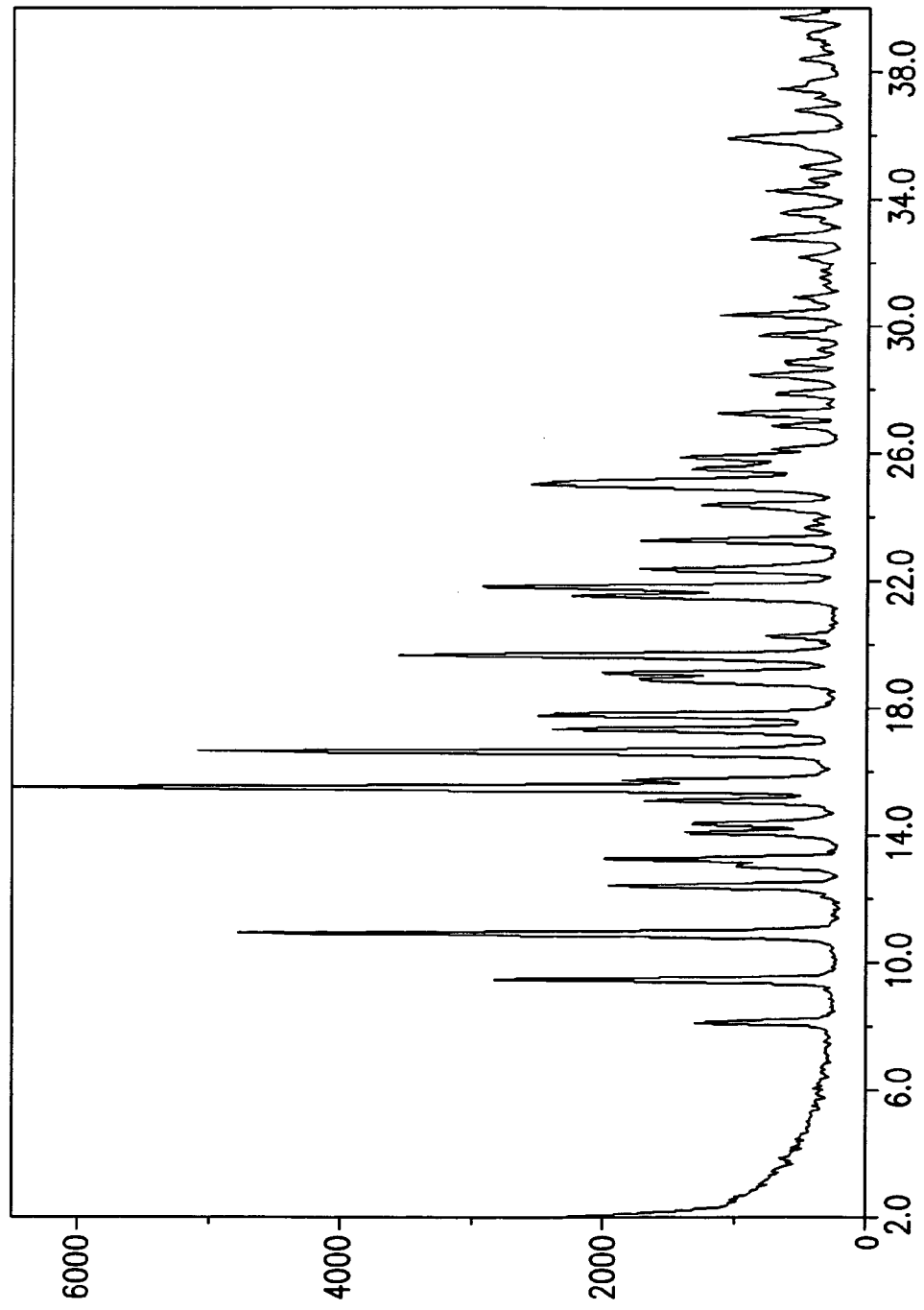
FIG. 4 illustrates a powder X-ray diffraction pattern of polymorphic pure crystalline Fluticasone furoate designated form A obtained in example 7.
Figure 5:
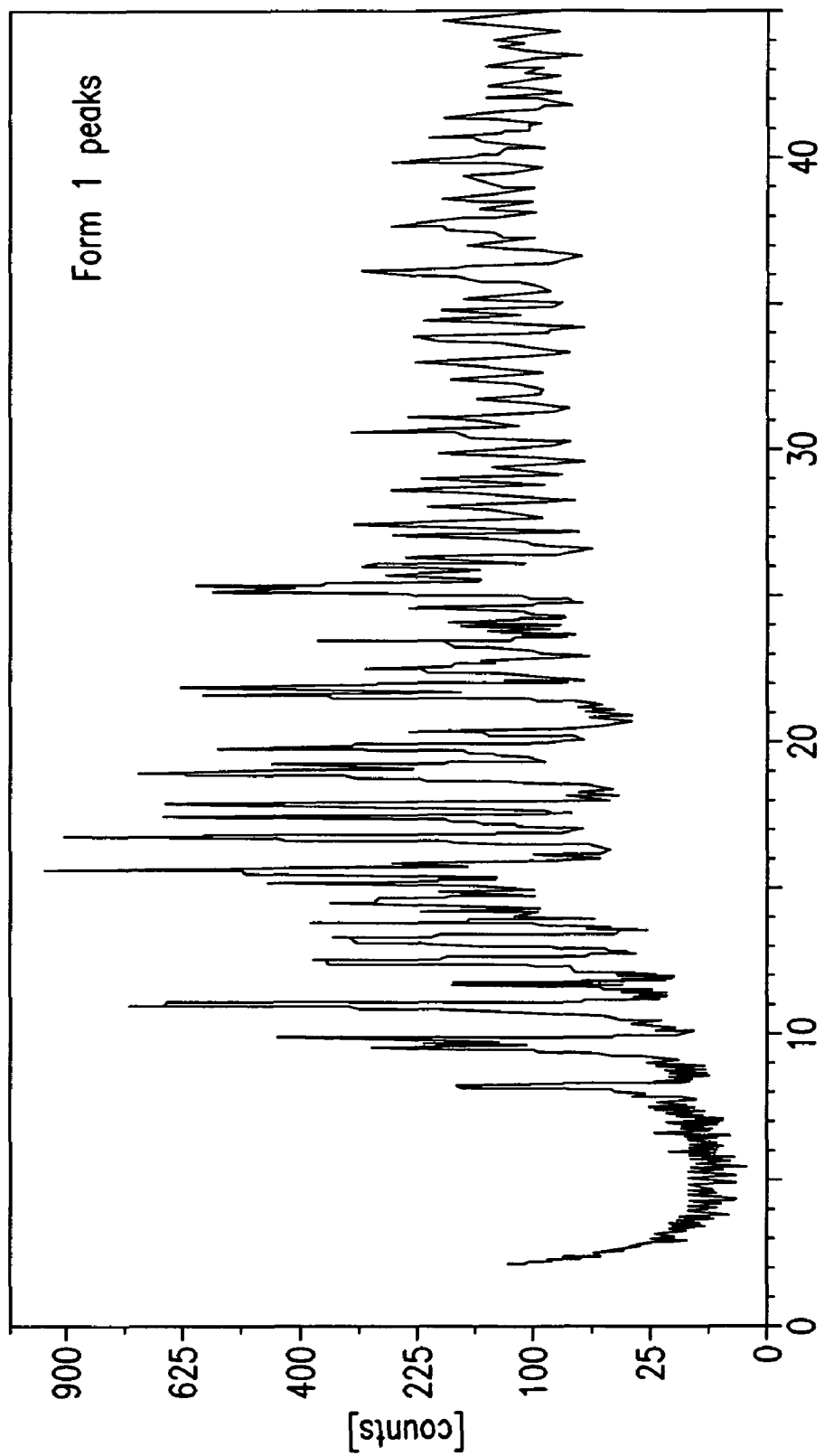
FIG. 5 illustrates a powder X-ray diffraction pattern of Fluticasone furoate THF solvate described in U.S. Pat. No. 6,777,399.
Figure 6:
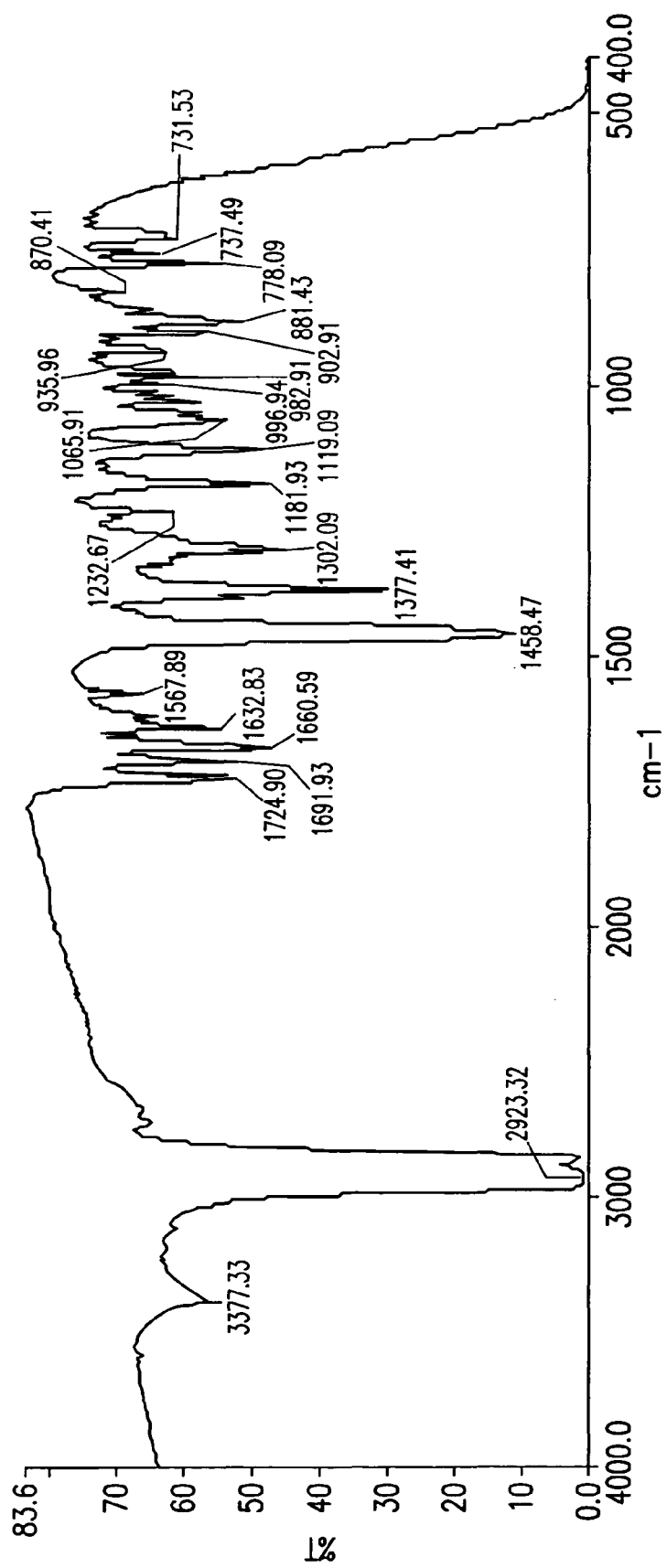
FIG. 6 illustrates a FT-IR pattern of crystalline Fluticasone furoate designated form A.

In another embodiment the present invention encompasses polymorphic pure crystalline form of Fluticasone furoate characterized by data selected from a group consisting of: powder XRD pattern having peaks at about 15.5, 16.6 and 18.8±0.2 degrees 2-theta and any 2 peaks selected from a list consisting of: 9.5, 10.9, 17.3, 17.8, 19.1, 19.7 and 21.8±0.2 degrees 2-theta; a powder XRD pattern having peaks at about 15.5, 16.6, 18.8, 19.1 and 21.8±0.2 degrees 2-theta; a PXRD pattern depicted in FIG. 3; a PXRD pattern depicted in FIG. 4; and any combination thereof. This crystalline form of Fluticasone furoate can be designated form A.

As used herein, unless mentioned otherwise, the term "polymorphic pure", in reference to the above crystalline Fluticasone furoate form A means crystalline Fluticasone furoate form A containing no more than about 10% by weight of crystalline Fluticasone furoate characterized by a powder XRD pattern with peaks at about 9.7, 11.6 and 13.7±0.2 degrees 2-theta, designated form 1, preferably not more than about 5%, more preferably not more than 1%.

Typically, the amount of form 1 in the crystalline Fluticasone furoate form A of the present invention can be measured by PXRD using any peak from the group of peaks at about: 9.7, 11.6 and 13.7±0.2 degrees two theta.

The above polymorphic pure crystalline form A of Fluticasone furoate can be further characterized by data selected from a group consisting of: A powder XRD pattern having peaks at about 9.5, 10.9, 17.3, 17.8 and 19.7±0.2 degrees 2-theta; FT-IR pattern having peaks at about 3379, 1724 and 1692 cm$^{-1}$ and any 2 peaks selected from a list consisting of: 1668, 1633, 1568, 1303, 1119, 983 and 882 cm$^{-1}$; a FT-IR pattern depicted in FIG. 4; a content of THF of about 12.7% to about 13.2% by weight as measured by TGA or by GC.

Preferably, the above form A of Fluticasone furoate is a tetrahydrofurane ("THF") solvate.

The above form A can be prepared by a process comprising crystallizing Fluticasone furoate from a mixture comprising ethyl acetate, water and THF.

Typically, the crystallization comprises dissolving a residue containing Fluticasone furoate and ethyl acetate in THF and precipitating the said crystalline form to obtain a suspension.

Preferably, prior to dissolving Fluticasone furoate in THF, a mixture comprising Fluticasone furoate, EtOAC and water is evaporated to obtain an oily residue.

Then, the concentrated mixture is then combined with THF, and the combination is heated to obtain the said solution. Preferably, heating is to about reflux temperature.

Preferably, precipitation is done by cooling the said solution to obtain a suspension comprising the said form A. Preferably, cooling is to about 20° C. Preferably, after cooling the suspension is further stirred. Preferably, stirring is performed at about room temperature. Preferably, stirring is performed for a period of about 2 hours.

The process for preparing crystalline form A may further comprise recovering the said crystalline form. The recovery may be done, for example, by filtering the suspension, washing and drying. Preferably, washing is done with THF. Preferably, drying is done by air. Preferably, drying is performed at room temperature.

The above process can further include an additional drying step.

Preferably, drying is done under vacuum. Preferably, drying is done at a temperature of about 100° C. Preferably, drying is done for a period of about 24 hours.

Figure 7:
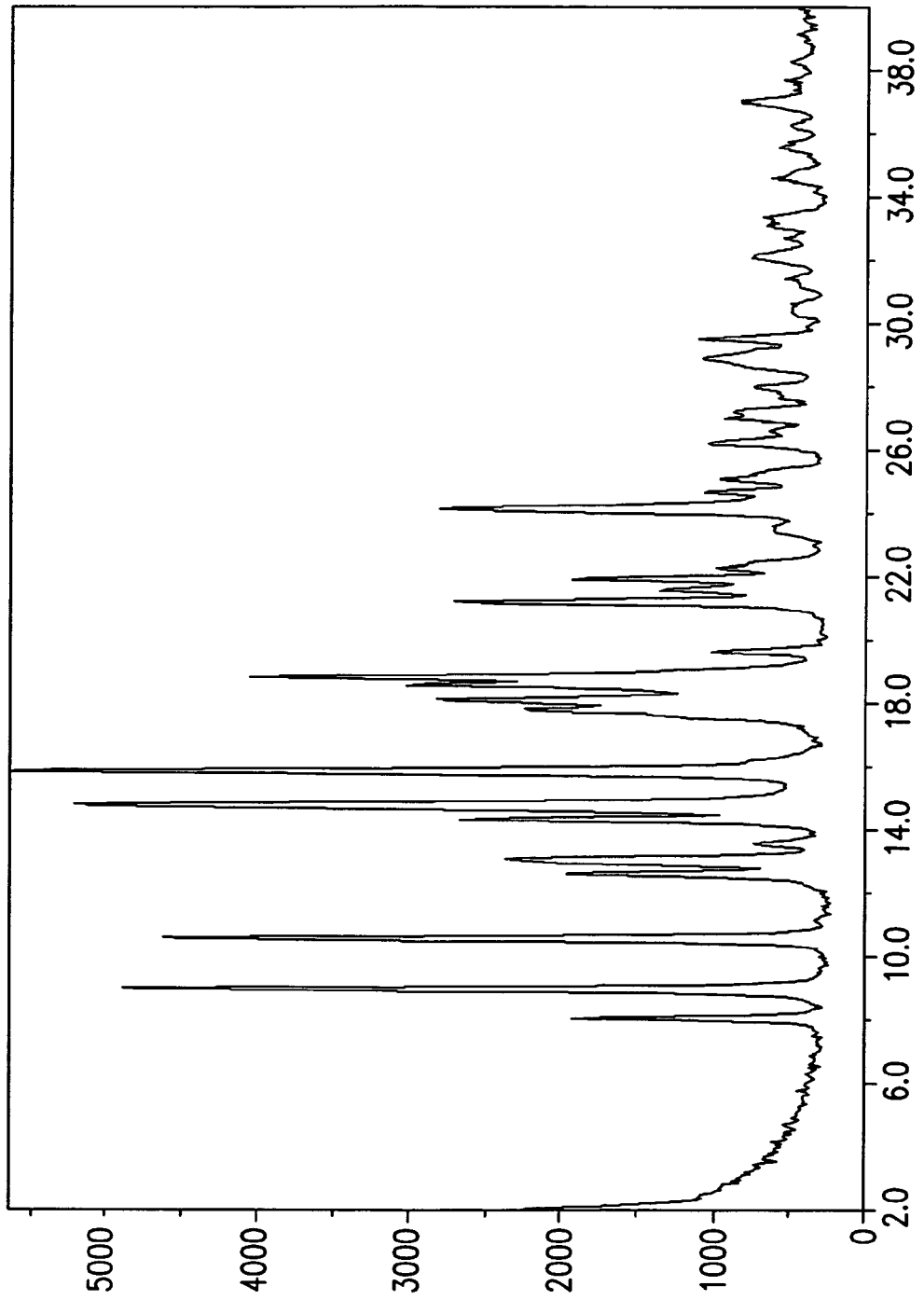
FIG. 7 illustrates a powder X-ray diffraction pattern of crystalline Fluticasone furoate designated form D.

In another embodiment, the present invention encompasses crystalline form of Fluticasone furoate characterized by data selected from a group consisting of: powder XRD pattern having peaks at about 9.0, 10.6, and 14.3±0.2 degrees two-theta, and any 2 peaks selected from a list consisting of: 14.8, 15.9, 17.8, 18.1, 18.6, 18.8 and 21.2±0.2 degrees 2-theta; a powder XRD pattern having peaks at about 9.0, 10.6, 14.3, 14.8 and 15.9±0.2 degrees two-theta; a PXRD pattern depicted in FIG. 7; and any combination thereof. This crystalline form of Fluticasone furoate can be designated form D.

Preferably, the above form D of Fluticasone furoate is a ter-butanol solvate.

Figure 8:
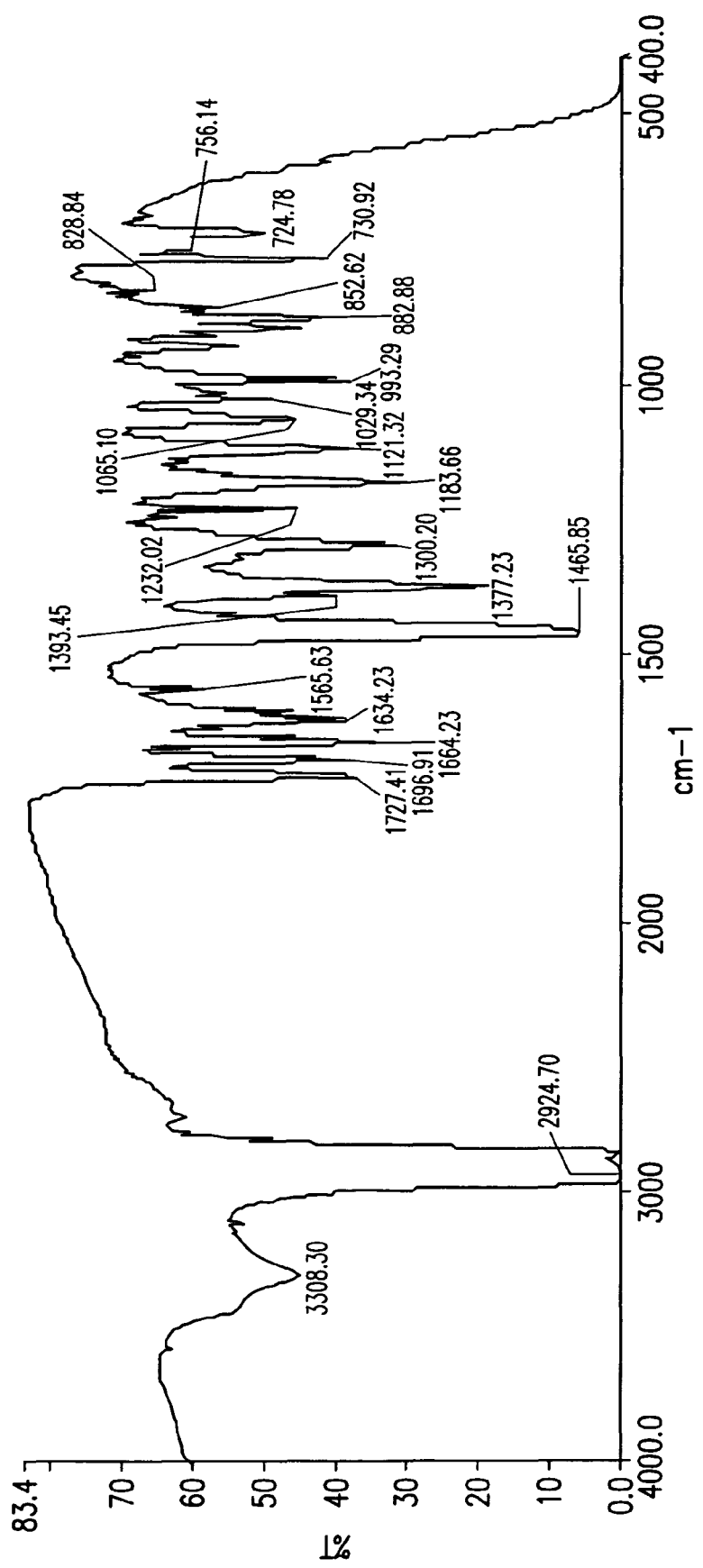
FIG. 8 illustrates a FT-IR pattern of crystalline Fluticasone furoate designated form D.

The above form D of Fluticasone furoate can be further characterized by data selected from a group consisting of: a powder XRD pattern having peaks at about 17.8, 18.1, 18.6, 18.8 and 21.2±0.2 degrees 2-theta; FT-IR pattern having peaks at about 3308, 1728, and 1697 $cm^{-1}$ and any 2 peaks selected from a list consisting of: 1664, 1624, 1561, 1300, 1184, 1121 and 993 $cm^{-1}$; a FT-IR pattern depicted in FIG. 8; and a content of tert-butanol of about 12.1% by weight as measured by TGA.

The above form D can be prepared by a process comprising suspending Fluticasone furoate DMAc solvate in tert-butanol at a temperature of about 60° C.

Preferably, prior to heating, Fluticasone furoate is suspended in tert-butanol at temperature of about room temperature.

The suspension can be stirred while being heated. Preferably, the stirring is for about 1 hour.

The process for preparing crystalline form D may further comprise recovery of the said crystalling form. The recovery may be done, for example, by filtering the suspension, washing and drying. Preferably, washing is done with 1-butanol. Preferably, drying is done under vacuum. Preferably, drying is performed at temperature of about 50° C. Preferably, drying is done for a period of about 16 hours.

Figure 9:
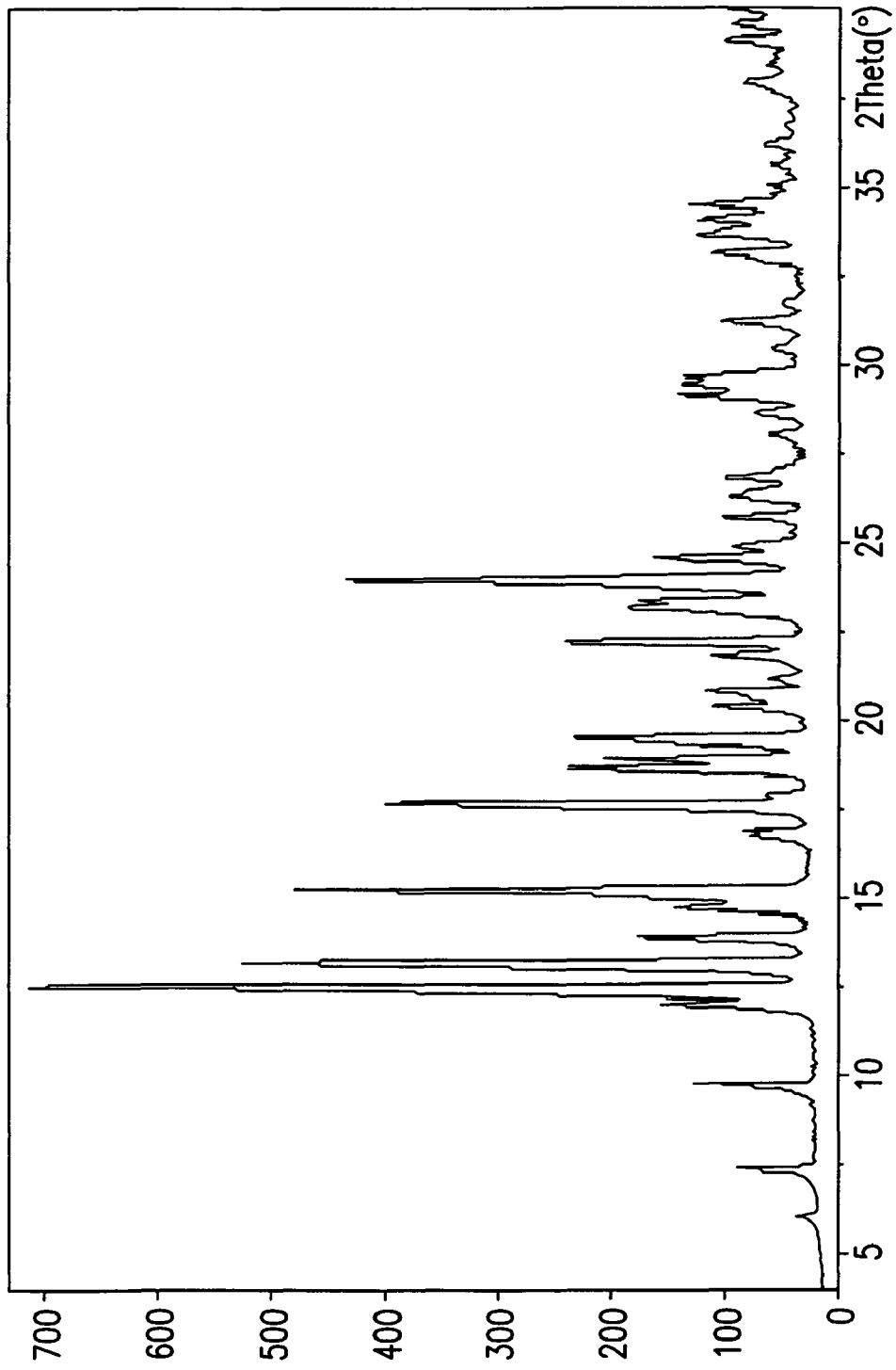
FIG. 9 illustrates a powder X-ray diffraction pattern of crystalline Fluticasone furoate designated form F obtained in example 9.
Figure 10:
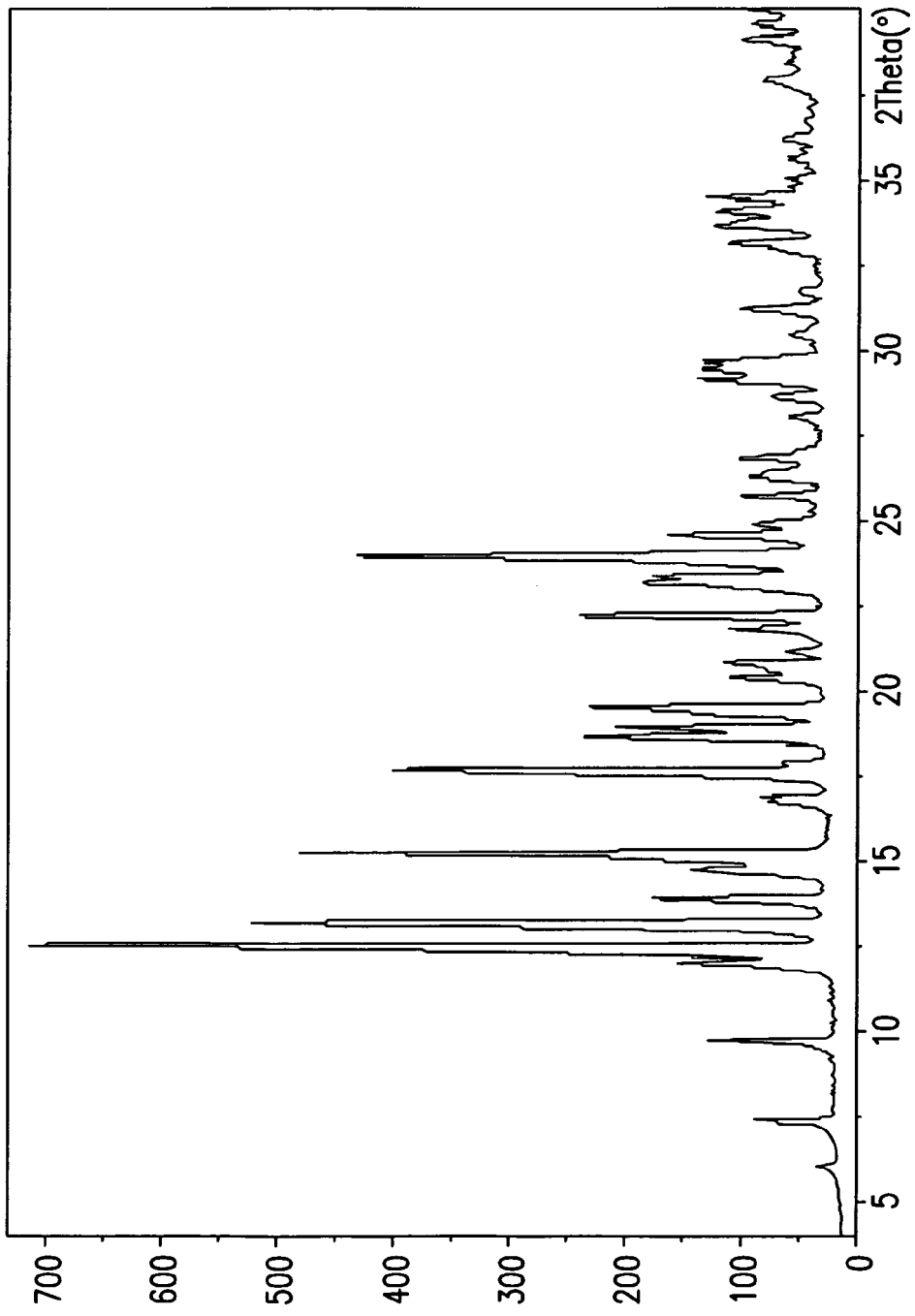
FIG. 10 illustrates a powder X-ray diffraction pattern of crystalline Fluticasone furoate designated form F obtained in example 10.

In another embodiment, the present invention encompasses crystalline form of Fluticasone furoate characterized by data selected from a group consisting of: powder XRD pattern having peaks at about 7.4, 12.5, and 17.7±0.2 degrees two-theta, and any 2 peaks selected from a list consisting of: 13.2, 15.3, 18.7, 19.6, 22.3 and 24.0±0.2 degrees 2-theta; a powder XRD pattern having peaks at about 7.4, 12.5, 15.3, 17.7 and 19.6±0.2 degrees two-theta; a PXRD pattern depicted in FIG. 9; a PXRD pattern depicted in FIG. 10; and any combination thereof. This crystalline form of Fluticasone furoate can be designated form F.

Preferably, the above form F of Fluticasone furoate is a 1,3 dimethylimidazolidinone ("DMI") solvate.

Figure 11:
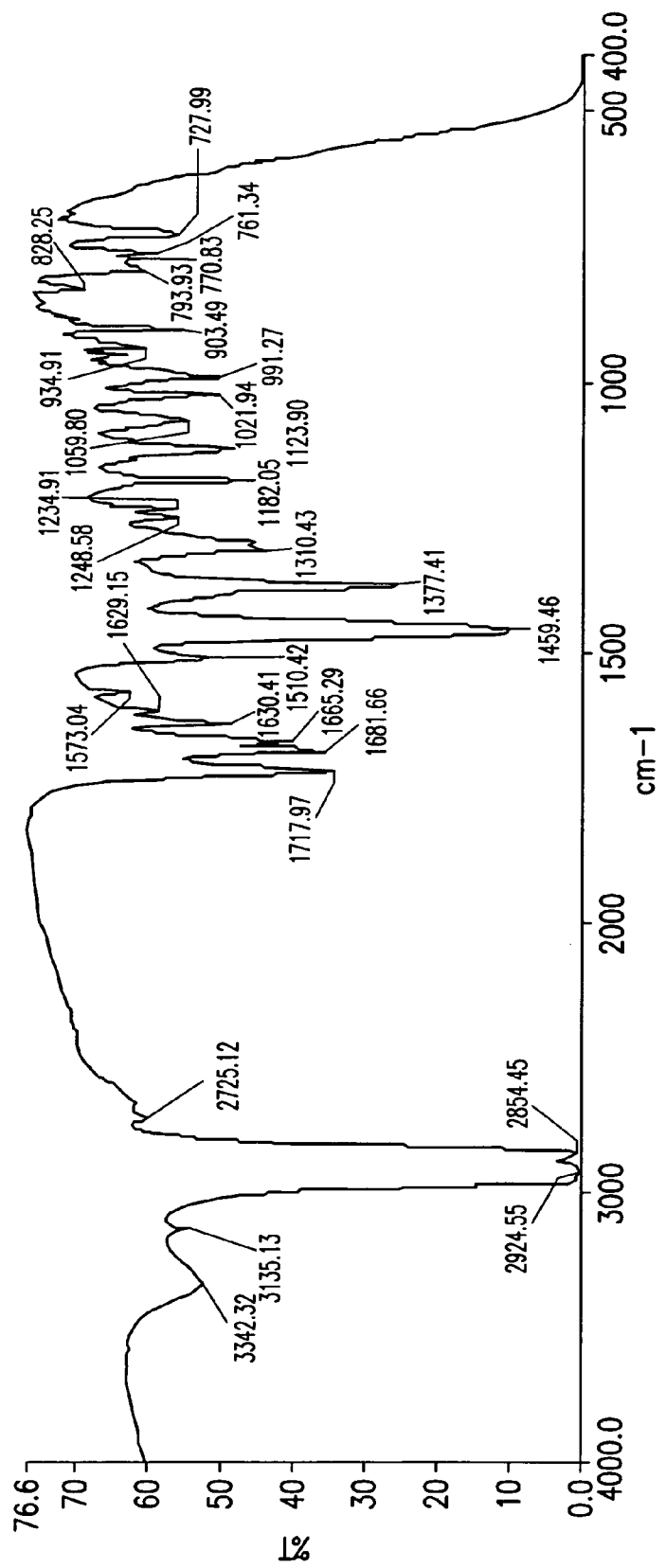
FIG. 11 illustrates a FT-IR pattern of crystalline Fluticasone furoate designated form F.

The above form F of Fluticasone furoate can be further characterized by data selected from a group consisting of: a powder XRD pattern having peaks at about 13.2, 18.7, 19.6, 22.3 and 24.0±0.2 degrees 2-theta; FT-IR pattern having peaks at about 3342, 1718, and 1682 $cm^{-1}$ and any 2 peaks selected from a list consisting of: 1665, 1630, 1510, 1310, 1182, 1124 and 991 $cm^{-1}$; a FT-IR pattern depicted in FIG. 11; a content of DMI of about 16.5% to about 21.8% by weight as measured by TGA and any combination thereof.

The above form F can be prepared by a process comprising crystallizing Fluticasone furoate from a mixture comprising DMI as a solvent and water as an anti-solvent.

The crystallization comprises providing a solution of the said Fluticasone furoate in DMI and combining the solution with water to obtain a suspension.

Preferably, the said solution is provided by combining Fluticasone furoate solvate and DMI and heating the said combination.

The starting Fluticasone furoate can be a Fluticasone furoate Dimethyl Foramide ("DMF") solvate or Dimethylacetamide ("DMAc") solvate that are obtained, for example, according to the process of U.S. Pat. No. 6,777,399 examples 5 and 15 respectively. Alternatively, the solution is a reaction mixture where Fluticasone furoate is formed. The synthesis can be done, for example, by the process of example 11.

Preferably, heating is done to a temperature of about 25° C. to about 110° C., more preferably about 25° C. to about 80° C., most preferably about 50° C. to about 80° C. Preferably, when using DMF solvate of Fluticasone furoate, heating is to a temperature of about 50° C. to about 80° C., more preferably about 80° C. Preferably, when using DMF solvate of Fluticasone furoate the obtained solution is cooled to a temperature of about 15° C. to about 80° C., prior to the addition of water, more preferably about 25° C. to about 50° C., most preferably 25° C.

Preferably, when using DMAc solvate of Fluticasone furoate, the dissolution is done at a temperature of about 25° C. to about 110° C., more preferably 50° C. to about 80° C. Further, the solution is cooled to a temperature of about 15° C. to about 80° C., prior to the addition of water. More preferably the solution is cooled to a temperature of about 25° C. to about 50° C., more preferably 50° C. Preferably, water is added to the solution at a temperature of about 50° C. Preferably, the addition of water is done drop-wise.

Preferably, when crystallizing Fluticasone furoate directly from the reaction mixture obtained in the synthesis process, i.e., without isolating the obtained crude Fluticasone furoate, the dissolution is done at a temperature of about 30° C. to about 100° C., more preferably 30° C. to about 50° C., most preferably about 30° C. to about 35° C. Further, water is added, and the obtained suspension is then cooled. Preferably, cooling is to a temperature of about −10° C. to about 20° C., preferably about 0° C. Preferably, cooling is done over a period of about 30 minutes to about 5 hours, more preferably 1 hour.

Preferably, the addition of water to the solution provides the suspension comprising the said crystalline form.

Preferably, the suspension is maintained, prior to recovering the said crystalline form. Preferably, maintaining is upon stirring. Preferably, the suspension is maintained at a temperature of about 0° C. to about 50° C., preferably at 25° C. to about 50° C. Preferably, when using DMF solvate the suspension is maintained at a temperature of about 25° C., preferably, for about 1 hour. Preferably, when using DMAc solvate of Fluticasone furoate the suspension is maintained at a temperature of about 50° C., preferably, for about 2 hours to about 3 hours, more preferably 2.5 hours.

The crystalline Fluticasone furoate form F obtained in the last step may further recovered. The recovery process may comprise filtering the said crystalling form, washing and drying. Preferably, washing is done with water. Preferably, drying is done either under nitrogen or by vacuum. Preferably, drying under nitrogen is done a temperature of about 35° C., preferably, for a period of about 2 hours. Preferably, drying by vacuum is done a temperature of about 60° C., preferably, for a period of about 16 hours.

Figure 12:
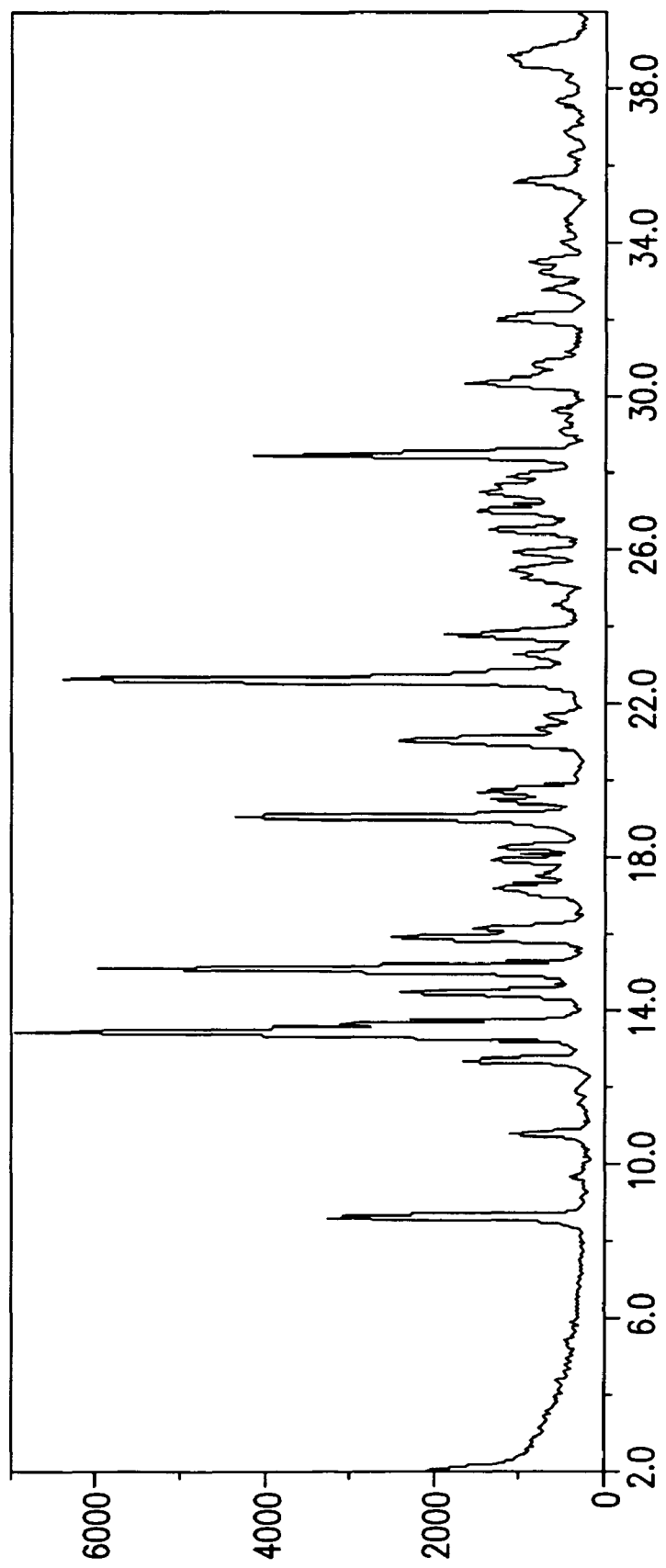
FIG. 12 illustrates a powder X-ray diffraction pattern of crystalline Fluticasone furoate designated form G.

In another embodiment, the present invention encompasses crystalline form of Fluticasone furoate characterized by data selected from a group consisting of: powder XRD pattern having peaks at about 8.6, 13.4, and 22.6±0.2 degrees two-theta, and any 2 peaks selected from a list consisting of: 10.8, 12.7, 14.5, 15.1, 19.0, 21.0 and 23.8±0.2 degrees 2-theta; a powder XRD pattern having peaks at about 8.6, 13.4, 15.1, 19.0 and 22.6±0.2 degrees two-theta; a PXRD pattern depicted in FIG. 12, and any combination thereof. This crystalline form of Fluticasone furoate can be designated form G.

Preferably, the above form G of Fluticasone furoate is a 1,3 Dimethyl-3,4,5,6-tetrahydro-2(1H)-pyrimidinone ("DMPU") solvate.

Figure 13:
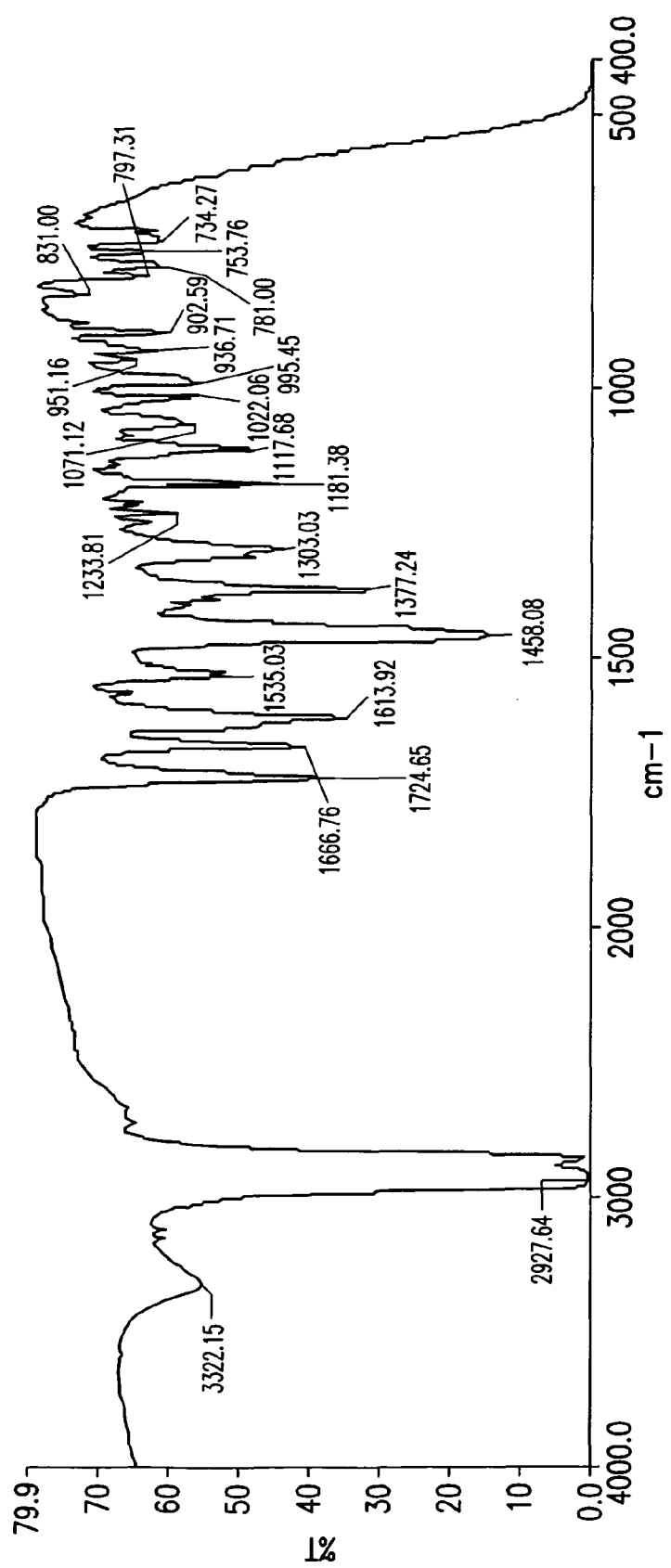
FIG. 13 illustrates a FT-IR pattern of crystalline Fluticasone furoate designated form G.

The above form G of Fluticasone furoate can be further characterized by data selected from a group consisting of: a powder XRD pattern having peaks at about 10.8, 12.7, 14.5, 21.0 and 23.8±0.2 degrees 2-theta; FT-IR pattern having peaks at about 1615, 1535, and 903 cm$^{-1}$ and any 2 peaks selected from a list consisting of: 3322, 1725, 1667, 1303, 1181, 1118 and 995 cm$^{-1}$; a FT-IR pattern depicted in FIG. 13; a content of DMPU of about 20.2% by weight as measured by TGA; and any combination thereof.

The above form G can be prepared by a process comprising crystallizing Fluticasone furoate from a mixture comprising DMPU as a solvent and water as an anti-solvent.

Preferably, the starting Fluticasone furoate that is anhydrous.

The crystallization comprises providing a solution of the said Fluticasone furoate in DMPU and combining the solution with water to obtain a suspension.

Preferably, the solution is provided by dissolving Fluticasone furoate in DMPU. Preferably, dissolving is at temperature of about 30° C. to about 100° C., more preferably, 30° C. to about 35° C., most preferably 30° C. Preferably cooling is done over a period of about 1 minute to about 30 minutes, more preferably 1 minute to about 2 minutes.

Preferably, the addition of water to the solution provides the suspension comprising the said crystalline form.

Preferably, the suspension is maintained, prior to recovering the said crystalline form. Preferably, maintaining is upon stirring. Preferably, the suspension is maintained at a temperature of about 0° C. to about 30° C. Preferably, maintaining is for a period of about 30 minutes to about 5 hours, more preferably 1 hour.

The recovery may be done, for example, by filtering the suspension, washing and drying.

Preferably, washing is done with water. Preferably, washing is done at a temperature of about 0° C. to about 35° C., more preferably 35° C., preferably for a period of about 1 hour to about 20 hours, more preferably 20 hours. Preferably, drying is done under nitrogen.

Figure 14:
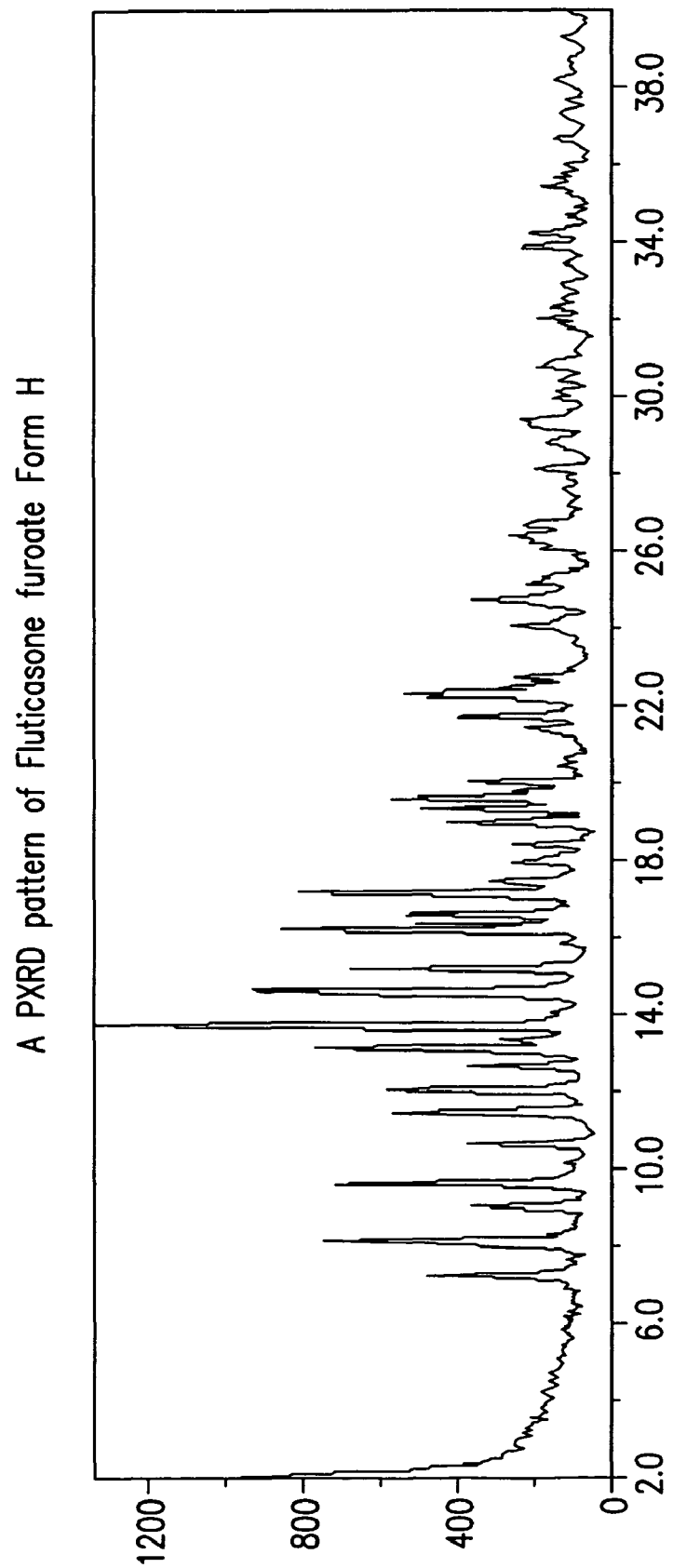
FIG. 14 illustrates a powder X-ray diffraction pattern of crystalline Fluticasone furoate designated form H.

In another embodiment, the present invention encompasses a crystalline form of Fluticasone furoate characterized by data selected from a group consisting of: powder XRD pattern having peaks at about 8.1, 9.6, 13.7, 14.6 and 15.2±0.2 degrees two-theta; a PXRD pattern depicted in FIG. 14; and any combination thereof. This crystalline form of Fluticasone furoate can be designated form H.

Preferably, the above form H of Fluticasone furoate is a 2-butanol solvate.

Figure 15:
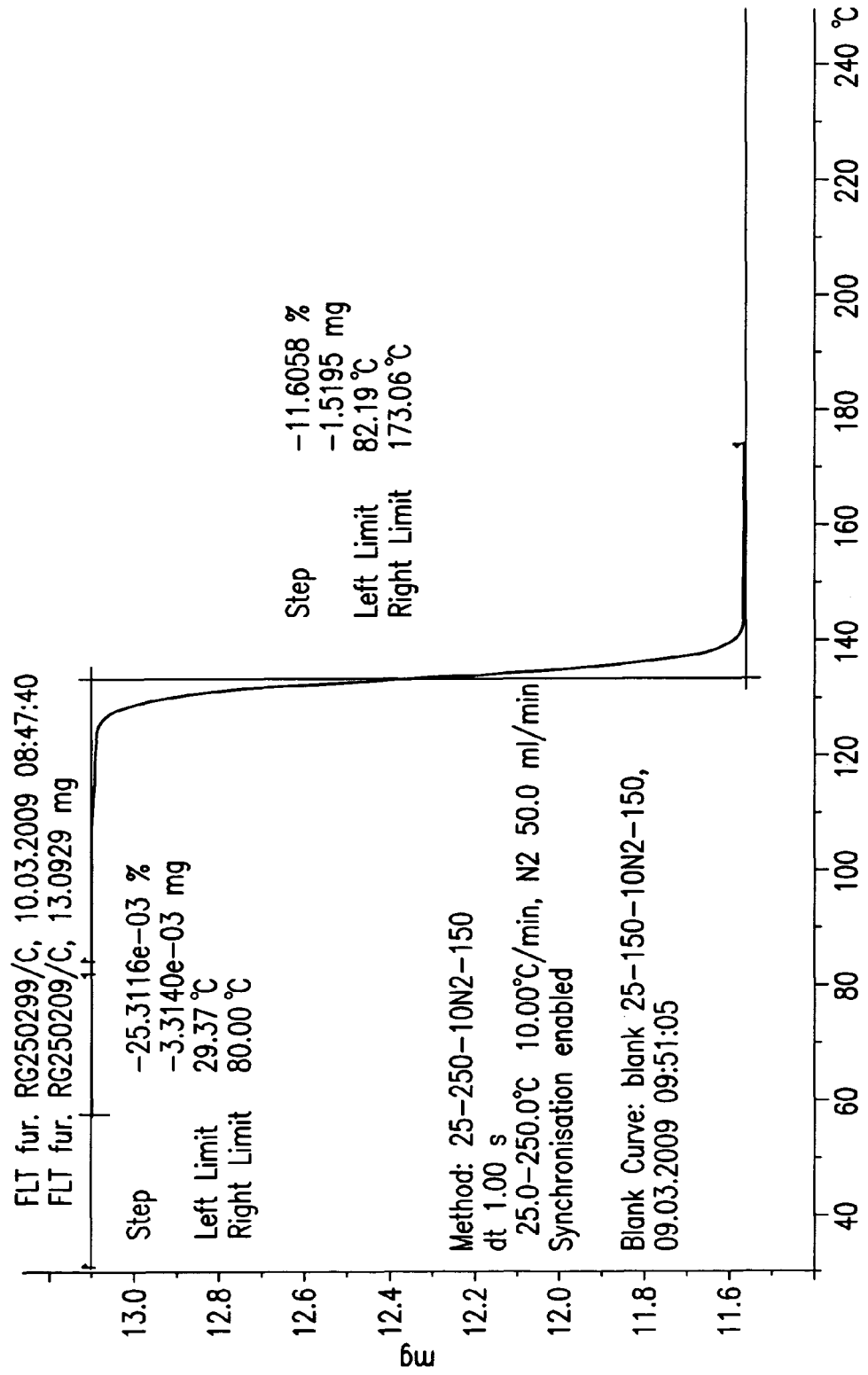
FIG. 15 illustrates a TGA pattern of crystalline Fluticasone furoate designated form H.

The above form H of Fluticasone furoate can be further characterized by data selected from a group consisting of: a powder XRD pattern having peaks at about 11.4, 12.0, 13.1, 16.2, and 17.1±0.2 degrees 2-theta; a weight loss of up to about 11.6% at a temperature range of 82° C. to 173° C. as measured by TGA, a TGA pattern as depicted in FIG. 15; a 2-butanol content of about 11.6% as measured by TGA; and any combination thereof.

The above form H can be prepared by a process comprising suspending Dimethylacetamide ("DMAc") solvate of Fluticasone furoate in 2-butanol.

First, a suspension is provided, preferably by combining DMAc solvate of Fluticasone furoate and 2-butanol to obtain a first suspension.

Then, the first suspension is cooled. Preferably, cooling is to a temperature of about 0° C., preferably, over a period of about 10 minutes.

Preferably, the suspension is further maintained after cooling, preferably upon stirring. Preferably, maintaining is done at a temperature of about 0° C., preferably for a period of about 10 minutes.

Afterwards, the maintained first suspension is heated, providing a second suspension. Preferably, heating is to a temperature of about 97° C., preferably for a period of about 1 hour.

Preferably, after heating the suspension is further maintained at the same temperature, preferably it is maintained upon stirring. Preferably, maintaining is for a period of about 10 minutes.

Further, the maintained second suspension is cooled, providing the said suspension. Typically, cooling is performed prior to performing a recovery process.

Preferably, cooling is to a temperature of about 0° C., preferably over a period of about 1 hour.

The said suspension can then be further maintained. Preferably, marinating is done upon stirring, preferably for a period of about 2 hours.

The recovery process may comprise, for example, filtering the said crystalline form and drying. Preferably drying is done under nitrogen. Preferably, drying is done at a temperature of about 35° C., preferably for a period of about 60 minutes.

Figure 16:
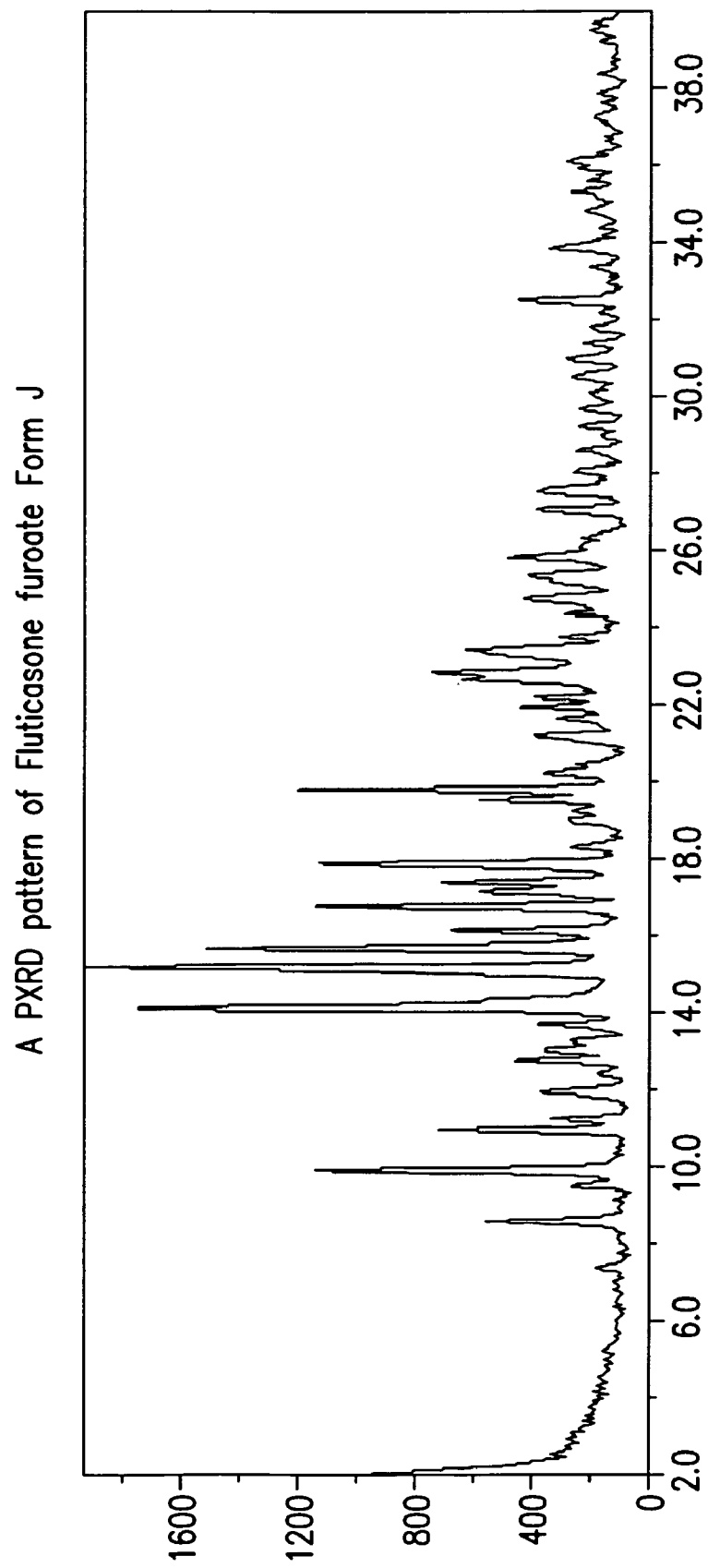
FIG. 16 illustrates a powder X-ray diffraction pattern of crystalline Fluticasone furoate designated form J.

In another embodiment, the present invention encompasses crystalline form of Fluticasone furoate characterized by data selected from a group consisting of: powder XRD pattern having peaks at about 9.9, 14.1, 15.1, 15.7 and 19.8±0.2 degrees two-theta; a PXRD pattern depicted in FIG. 16, and any combination thereof. This crystalline form of Fluticasone furoate can be designated form J.

Preferably, the above form J of Fluticasone furoate is a 1,3-dioxolane solvate.

Figure 17:
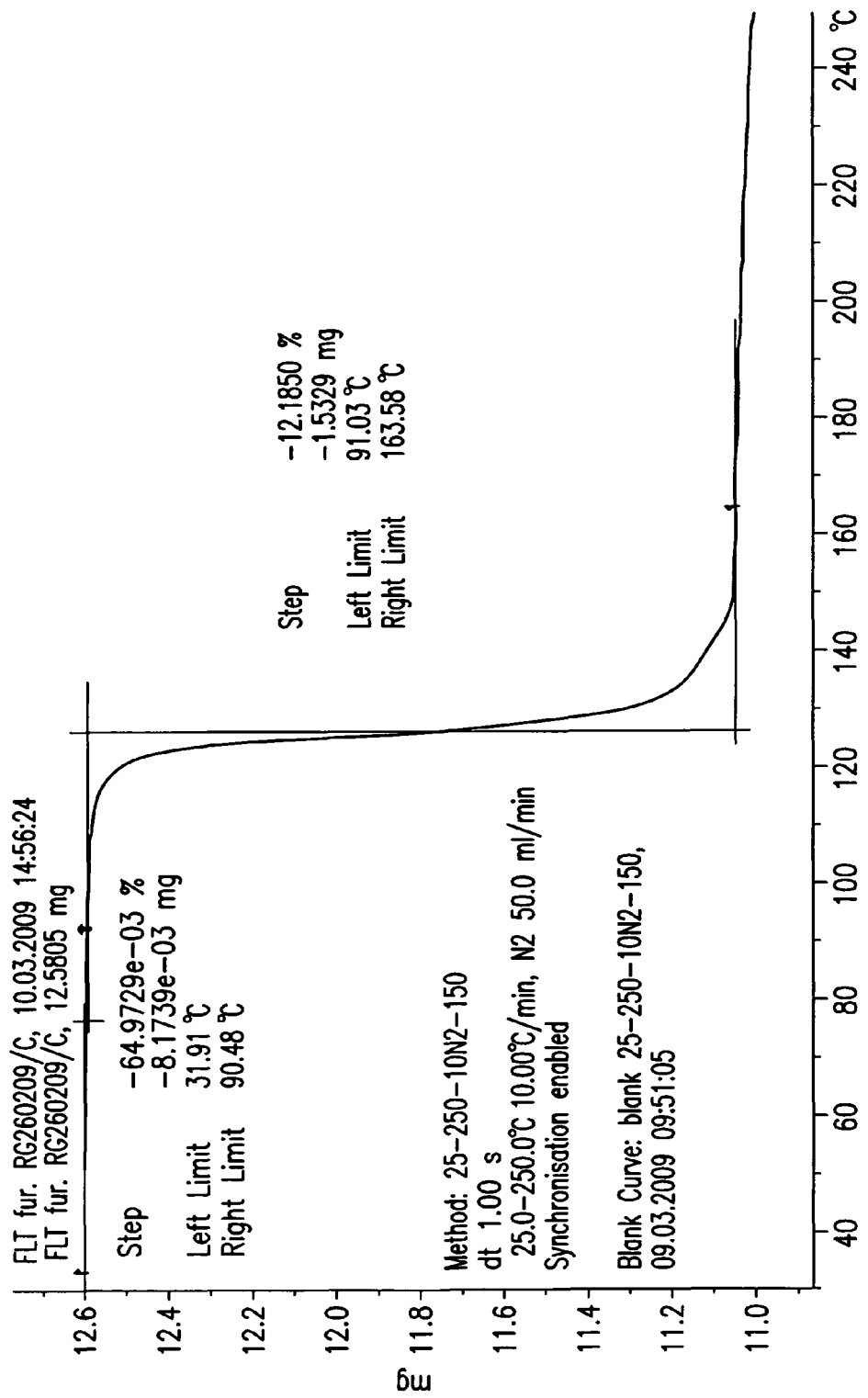
FIG. 17 illustrates a TGA pattern of crystalline Fluticasone furoate designated form J.

The above form J of Fluticasone furoate can be further characterized by data selected from a group consisting of: a powder XRD pattern peaks at about 10.9, 16.8, 17.9 and 23.4; a weight loss of up to about 12.2% at a temperature range of 90° C. to 163° C. as measured by TGA, a TGA pattern as depicted in FIG. 17; a 1,3-dioxalane content of about 12.2% as measured by TGA; and any combination thereof.

The above form J can be prepared by a process comprising crystallizing the said form from a solution of 1,3-dioxalane.

Typically, the crystallization comprises providing a solution of Fluticasone furoate in 1,3-dioxane and precipitating to obtain a suspension comprising the said form J.

The said solution is provided, preferably by combining Fluticasone furoate to obtain a first suspension and heating the said first suspension to obtain a solution.

Preferably, the first suspension is cooled prior to heating. Preferably, cooling is to a temperature of about 0° C., preferably, over a period of about 10 minutes. Preferably, the first suspension is further maintained after cooling, preferably upon stirring. Preferably, maintaining is done at a temperature of about 0° C., preferably for a period of about 10 minutes.

Then, the said first suspension is heated to obtain the said solution. Preferably, heating is to a temperature of about 44° C., preferably for a period of about 45 minutes. After the said solution is formed, it is cooled to obtain the said suspension, comprising Fluticasone furoate form J.

Preferably, cooling is to a temperature of about 0° C., preferably over a period of about 1 hour.

The said suspension can then be further maintained. Preferably, marinating is done upon stirring, preferably for a period of about 2 hours.

The recovery process may comprise, for example, filtering the said crystalline form and drying. Preferably drying is done under nitrogen. Preferably, drying is done at a temperature of about 35° C., preferably for a period of about 60 minutes.

Figure 18:
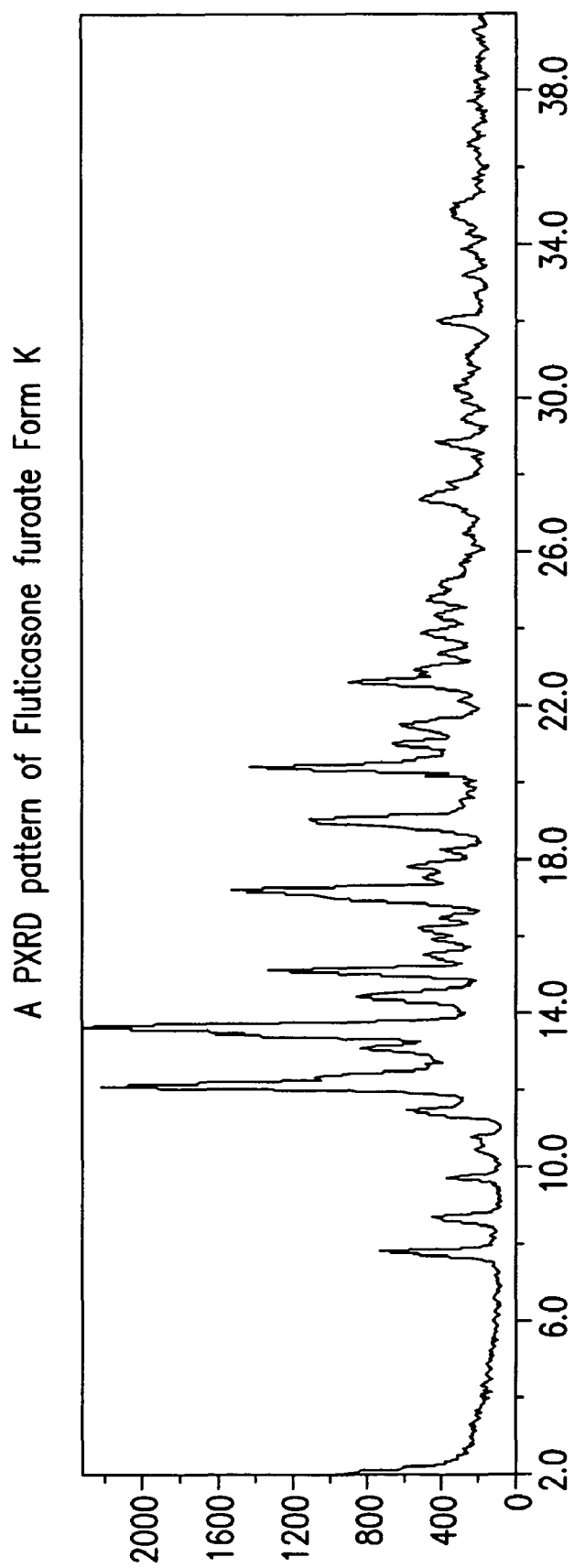
FIG. 18 illustrates a powder X-ray diffraction pattern of crystalline Fluticasone furoate designated form K.

In another embodiment, the present invention encompasses crystalline form of Fluticasone furoate characterized by data selected from a group consisting of: powder XRD pattern having peaks at about 12.1, 13.6, 15.1, 17.1 and 20.4±0.2 degrees two-theta; a PXRD pattern depicted in FIG. 18; and any combination thereof. This crystalline form of Fluticasone furoate can be designated form K.

Preferably, the above form K of Fluticasone furoate is a 1,3 Dimethyl-3,4,5,6-tetrahydro-2(1H)-pyrimidinone ("DMPU") solvate.

Figure 19:
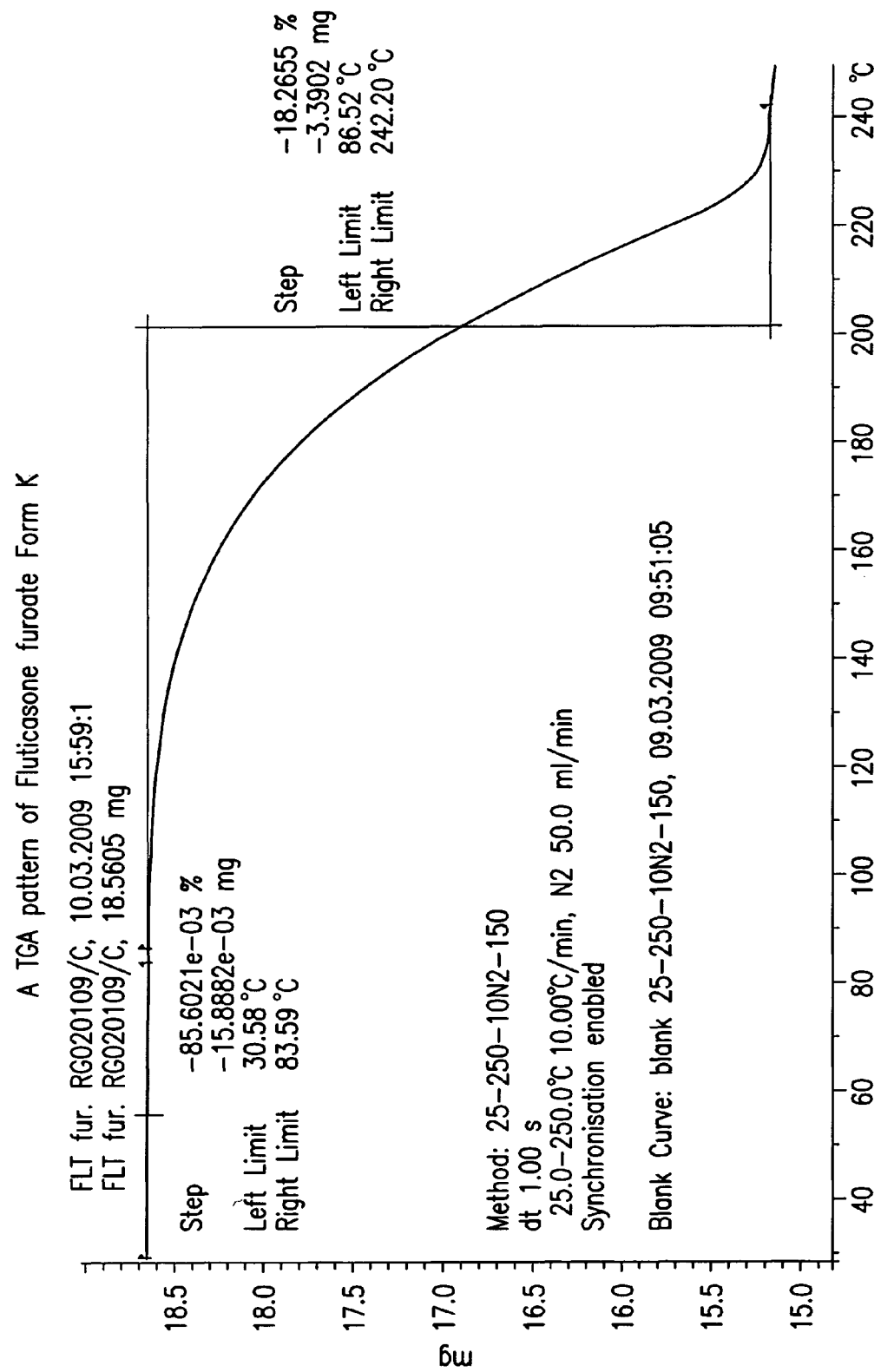
FIG. 19 illustrates a TGA pattern of crystalline Fluticasone furoate designated form K.

The above form K of Fluticasone furoate can be further characterized by can be further characterized by data selected from a group consisting of: a powder XRD pattern having Peaks at about 7.8, 14.4, 19.0, 21.0 and 22.6±0.2 degrees 2-theta; a weight loss of up to about 18.3% at a temperature range of 86° C. to 242° C. as measured by TGA; a TGA pattern as depicted in FIG. 19; a DMPU content of about 18.3% as measured by TGA; and any combination thereof.

The above form K can be prepared by a process comprising crystallizing Fluticasone furoate from a mixture comprising 1,3 Dimethyl-3,4,5,6-tetrahydro-2(1H)-pyrimidinone ("DMPU") as a solvent and water as an anti-solvent.

The crystallization comprises providing a solution of the said Fluticasone furoate in DMPU and combining the solution with water to obtain a suspension comprising the said for K.

Preferably, the said solution is provided by combining Fluticasone furoate solvate and DMPU and heating the said combination.

Preferably, the solution is heated to a temperature of about 50° C.

Then, water is added to the solution to obtain a suspension comprising the said form. Preferably, water is added drop-wise. Preferably, water is added while heating the solution, preferably to a temperature of about 50° C.

The suspension can be maintained at the same temperature prior to the recovery of Fluticasone furoate form K from the suspension.

Preferably, marinating is done upon stirring, preferably for a period of about 2.5 hours.

The recovery process may comprise, for example, filtering the said crystalline form and drying. Preferably drying is done under nitrogen. Preferably, drying is done at a temperature of about 35° C., preferably for a period of about 60 minutes.

Figure 20:
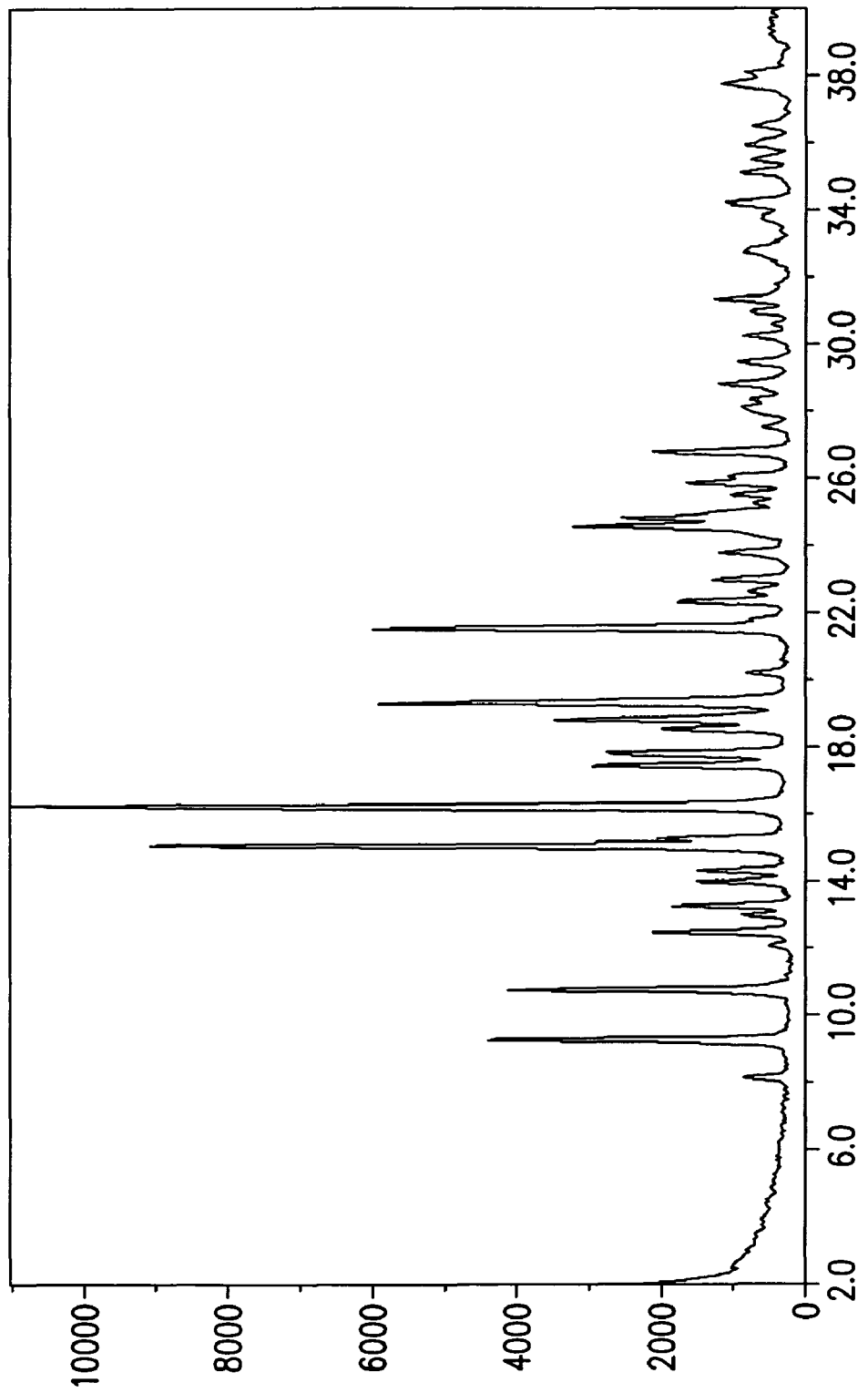
FIG. 20 illustrates a powder X-ray diffraction pattern of crystalline Fluticasone furoate designated form B.

The present invention also describes crystalline Fluticasone furoate characterized by data selected from a group consisting of: powder XRD pattern having peaks at about 9.3, 15.1, and 16.2±0.2 degrees two-theta, and any 2 peaks selected from a list consisting of: 10.8, 17.5, 17.8, 19.3, 21.6, 24.6, and 24.8±0.2 degrees 2-theta; a powder XRD pattern having peaks at about 9.3, 10.8, 15.1, 16.2 and 19.3±0.2 degrees two-theta; a PXRD pattern depicted in FIG. 20, and any combination thereof. This crystalline form of Fluticasone furoate can be designated form B.

Preferably, the above form B of Fluticasone furoate is a 1,4-dioxane solvate.

Figure 21:
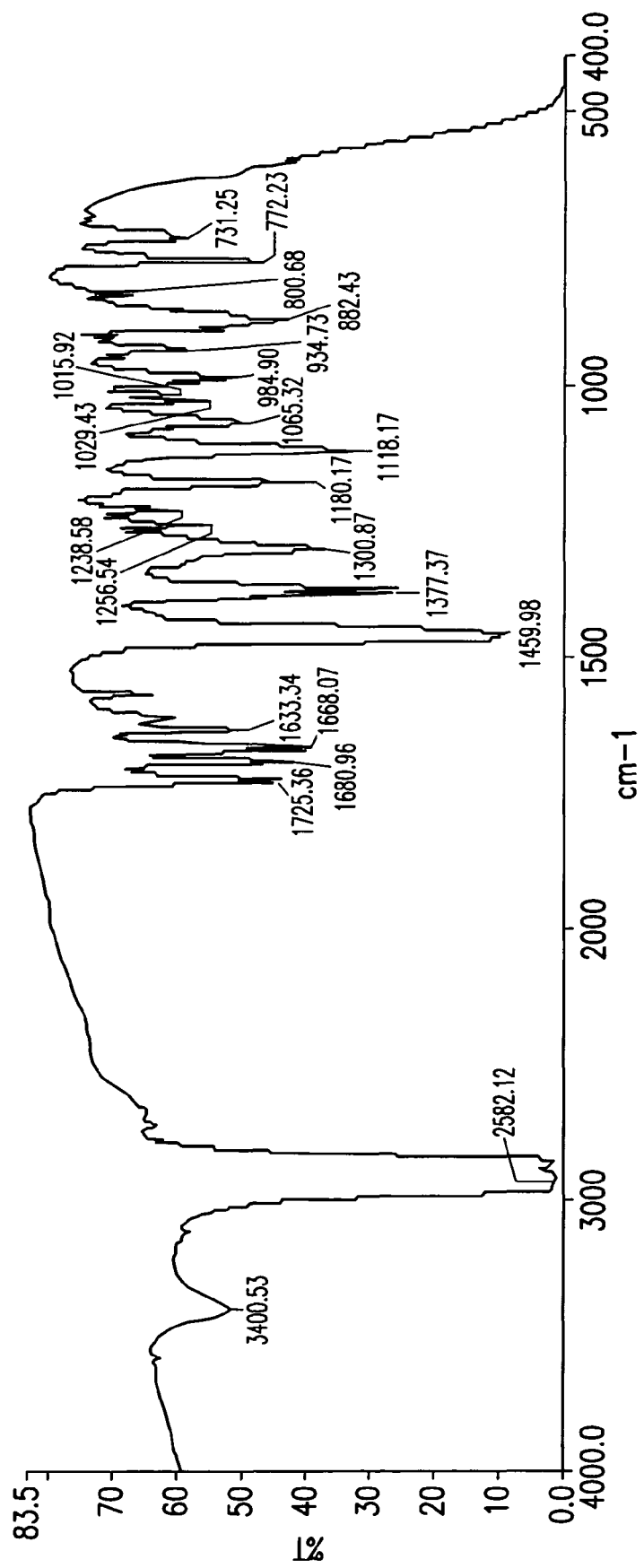
FIG. 21 illustrates a FT-IR pattern of crystalline Fluticasone furoate designated form B.

The above form B of Fluticasone furoate can be further characterized by data selected from a group consisting of: A powder XRD pattern having peaks at about 17.5, 17.8, 21.6, 24.6 and 24.8±0.2 degrees 2-theta; FT-IR pattern having peaks at about 3401, 1725, and 1633 cm$^{-1}$ and any 2 peaks selected from a list consisting of: 1691, 1668, 1610, 1568, 1301, 1180 and 1118 cm$^{-1}$; a FT-IR pattern depicted in FIG. 21; a content of 1,4-dioxane of about 14.7% by weight as measured by TGA; and any combination thereof.

The above form B can be prepared by a process comprising crystallizing Fluticasone furoate from a mixture comprising 1,4-dioxane and water.

Preferably, the crystallization comprises providing a solution comprising Fluticasone furoate, 1,4-dioxane and water, and precipitating the said crystalline form B to obtain a suspension.

Preferably, the Fluticasone furoate provided to the solution is anhydrous Preferably, the said solution is obtained by combining Fluticasone furoate, 1,4-dioxane and water, and heating the said combination. Preferably, heating is done to a temperature of about 60° C.

Preferably, precipitation is done by combining the said solution with water. Preferably, the water is added to the solution. Preferably, the addition of water to the solution is done drop-wise.

Figure 22:
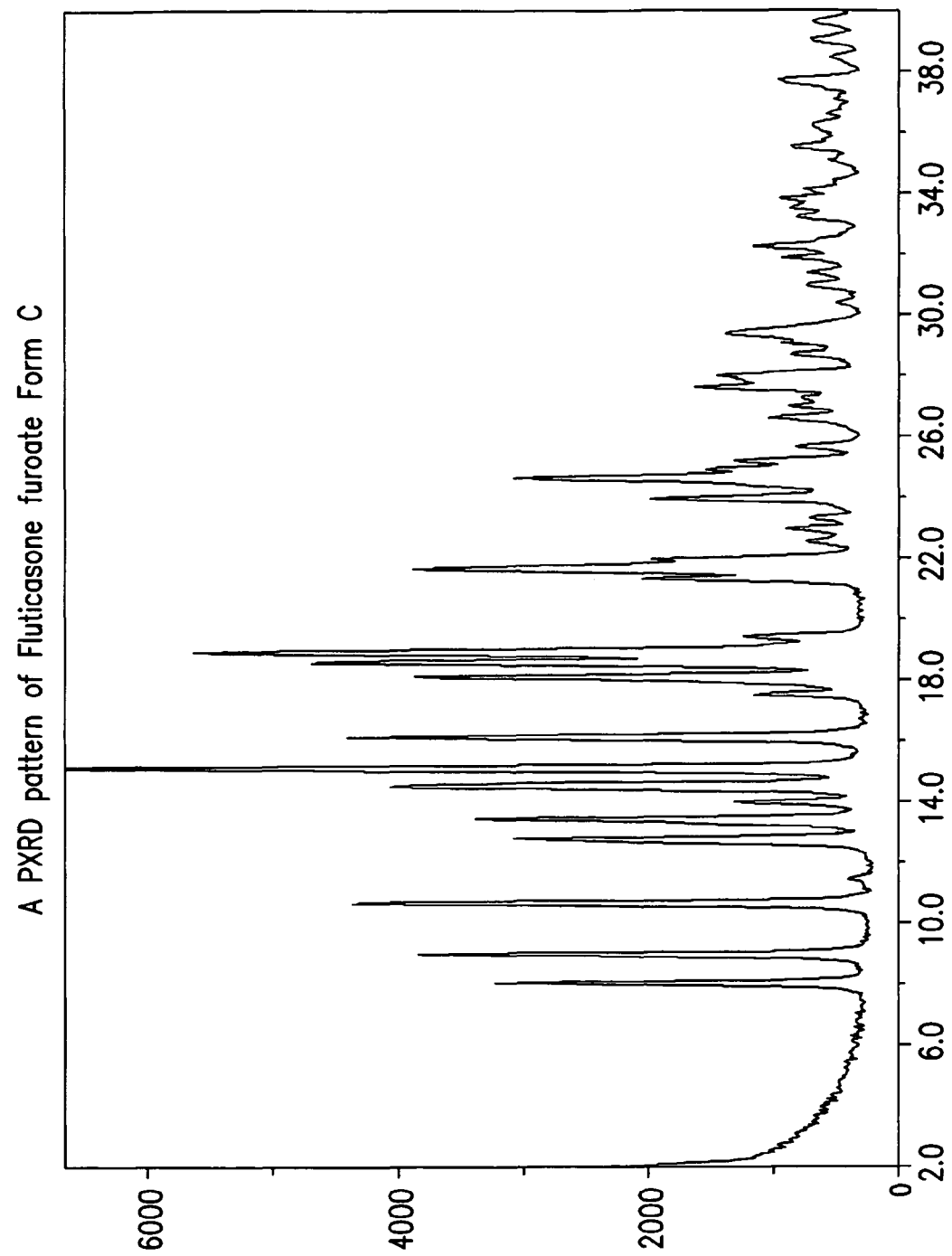
FIG. 22 illustrates a powder X-ray diffraction pattern of crystalline Fluticasone furoate designated form C.

The process for preparing crystalline form B may further comprise recovery of the said crystalline form. The recovery may be done, for example, by cooling the suspension, filtering, washing and drying. Preferably, washing is done with water. Preferably, drying is done by air. Preferably, drying is performed at room temperature The present invention also describes crystalline form of Fluticasone furoate characterized the PXRD pattern as depicted in FIG. 22. This solvate can be designated form C.

Preferably, the above form C of Fluticasone furoate is a 1-butanol solvate.

The above form C of Fluticasone furoate can be further characterized by a content of 1-butanol of about 12.1% by weight as measured by TGA.

The above form C can be prepared by a process comprising suspending Fluticasone furoate DMAc solvate in 1-butanol.

Preferably, the suspension is provided at temperature of about room temperature.

Preferably, the suspension is stirred, preferably, for about 24 hours.

The process for preparing crystalline form C may further comprise recovery of the said crystalline form. The recovery may be done, for example, by filtering the suspension, washing and drying. Preferably, washing is done with 1-butanol. Preferably, drying is done under vacuum. Preferably, drying is performed at temperature of about 50° C. Preferably, drying is done for a period of about 16 hours.

Figure 23:
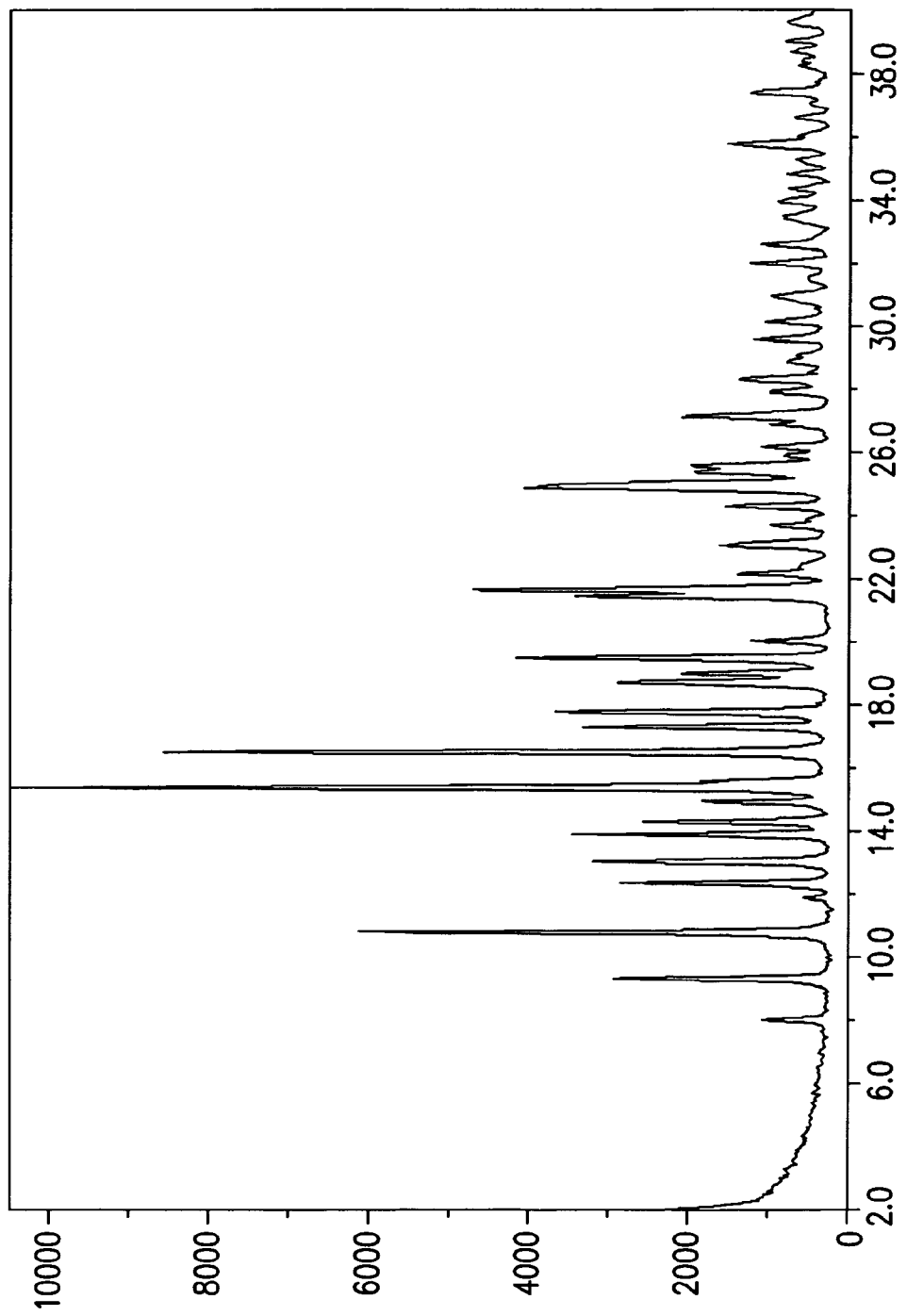
FIG. 23 illustrates a powder X-ray diffraction pattern of crystalline Fluticasone furoate designated form E.

In another embodiment, the present invention encompasses crystalline form of Fluticasone furoate characterized by data selected from a group consisting of: powder XRD pattern having peaks at about 12.3, 13.0, and 13.9±0.2 degrees two-theta, and any 2 peaks selected from a list consisting of: 9.3, 10.8, 15.4, 16.5, 19.5, 21.7 and 25.4±0.2 degrees 2-theta; a powder XRD pattern having peaks at about 9.3, 12.3, 13.0, 13.9 and 15.4±0.2±0.2 degrees two-theta; a PXRD pattern depicted in FIG. 23, and any combination thereof. This crystalline form of Fluticasone furoate can be designated form E.

Preferably, the above form E of Fluticasone furoate is a pyridine solvate.

Figure 24:
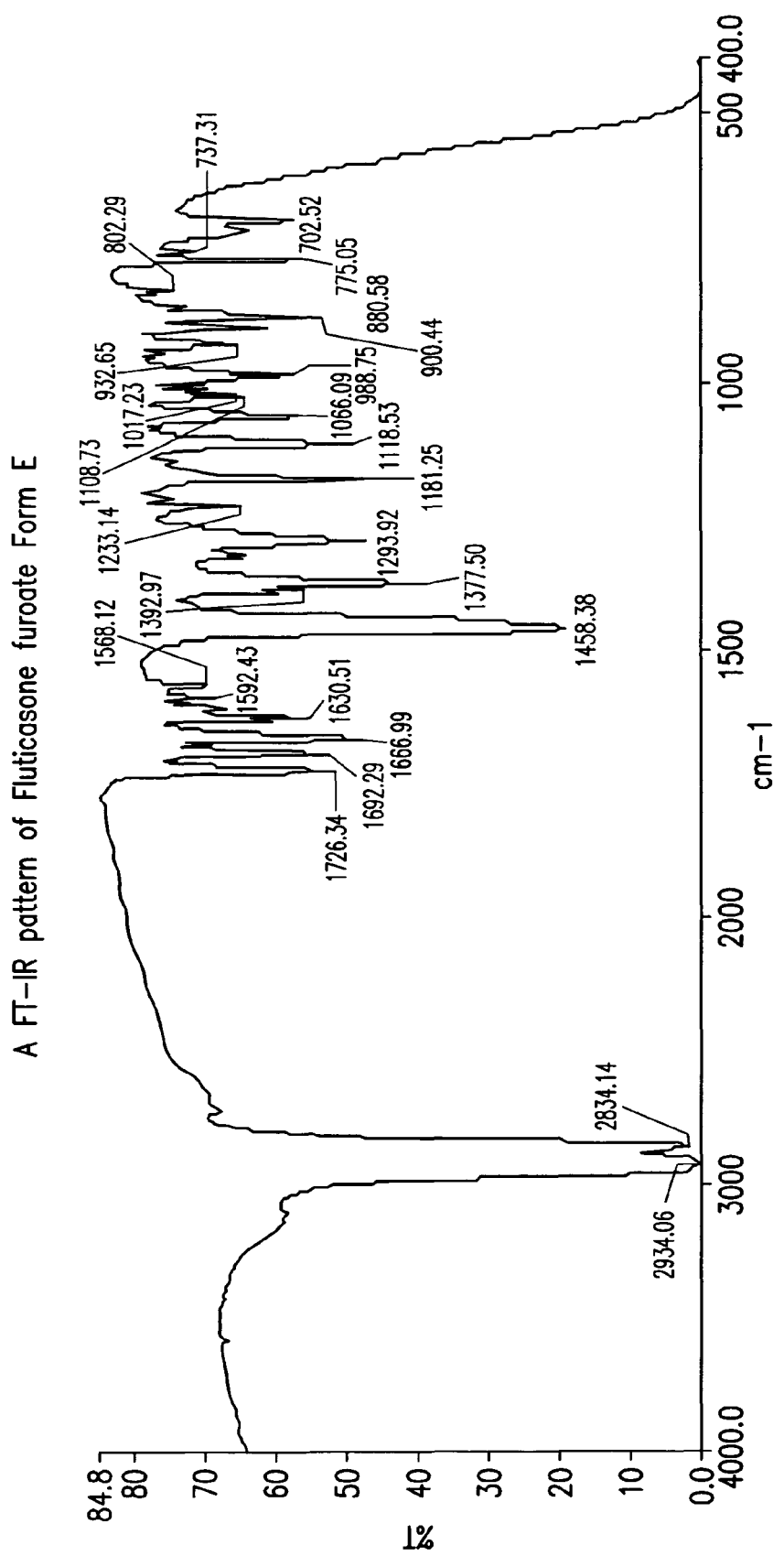
FIG. 24 illustrates a FT-IR pattern of crystalline Fluticasone furoate designated form E.

The above form E of Fluticasone furoate can be further characterized by data selected from a group consisting of: 10.8, 16.5, 19.5, 21.7 and 25.4±0.2 degrees 2-theta; FT-IR pattern having peaks at about 1726, 1692, and 1667 cm$^{-1}$ and any 2 peaks selected from a list consisting of: 1631, 1610, 1568, 1299, 1181, 989 and 881 cm$^{-1}$; a FT-IR pattern depicted in FIG. 24; a content of pyridine of about 13.4% by weight as measured by TGA; and any combination thereof.

The above form E can be prepared by a process comprising: reacting 6α,9α-Difluoro-17α-(2-furanylcarbonyl)oxy)-11β-hydroxy-16α-methyl-3-oxo-androsta-1,4-diene-17β-carbothionic acid, a Fluticasone furoate intermediate 1, of the following formula:

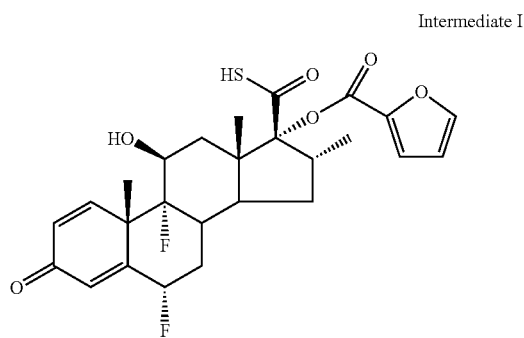

Intermediate I pyridine and bromofluoromethane to obtain a suspension comprising the said crystalline form E.

Preferably, said reaction is done in the presence of a solvent, preferably the solvent is DMAc.

Preferably, bromofluoromethane is dissolved prior to reacting with pyridine. Preferably, the solvent is DMAc Preferably, the said suspension is stirred. Preferably, stirring is performed at about room temperature, preferably, for a period of about 4 hours.

The process for preparing crystalline form E may further comprise recovery of the said crystalline form. The recovery may be done, for example, by combining the suspension with water to obtain a mixture, filtering the mixture, washing and drying. Preferably, washing is done by water. Preferably, drying is done by air. Preferably, drying is performed at about room temperature.

Preferably, drying is done to a constant weight. Preferably said constant weight is of about 5.7 gr.

Figure 25:
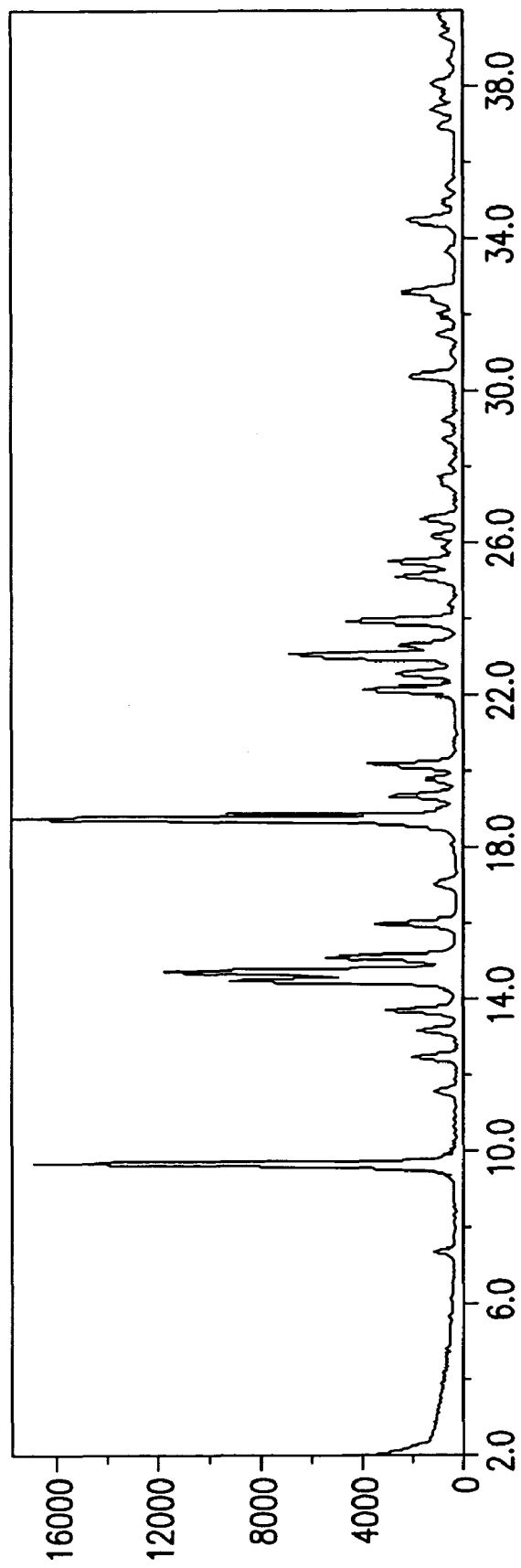
FIG. 25 illustrates a powder X-ray diffraction pattern of crystalline Fluticasone furoate designated form 5.

The present invention also describes crystalline Fluticasone furoate characterized by data selected from a group consisting of: powder XRD pattern having peaks at about 9.7, 14.7, 15.1, 18.8 and 24.0±0.2 degrees two-theta; a PXRD pattern depicted in FIG. 25; and any combination thereof. This crystalline form of Fluticasone furoate can be designated form 5.

Figure 26:
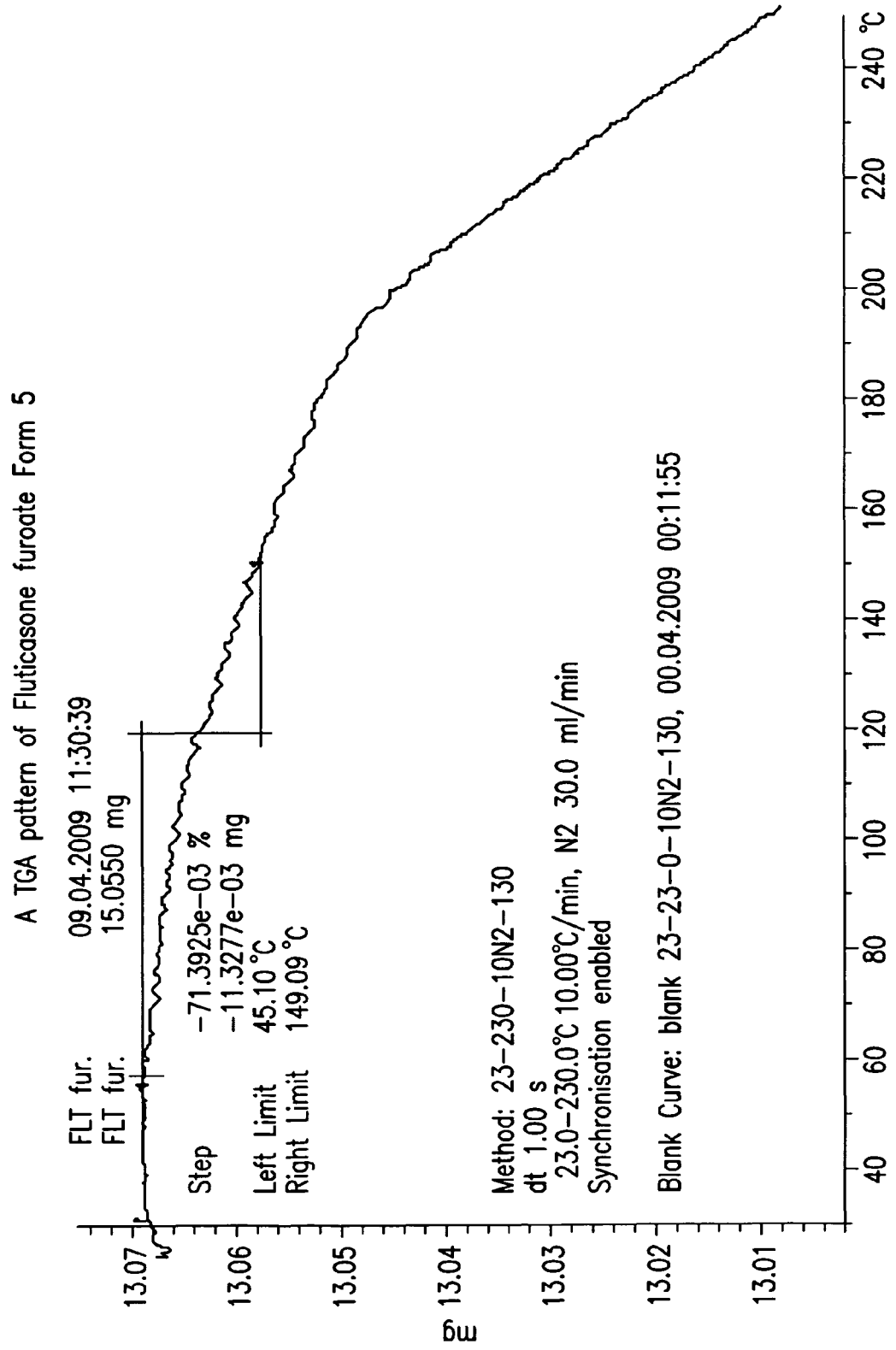
FIG. 26 illustrates a TGA pattern of crystalline Fluticasone furoate designated form 5.

The above form 5 of Fluticasone furoate can be further characterized by data selected from a group consisting of: a powder XRD pattern having peaks at about 13.7, 16.0, 20.2, 22.2 and 23.1±0.2 degrees 2-theta; a weight loss of less than about 0.2% at a temperature of up to 150° C. as measured by TGA; a TGA pattern as depicted in FIG. 26; and any combination thereof.

The above form 5 can be prepared by a process comprising suspending Dimethylacetamide ("DMAc") solvate of Fluticasone furoate in a solvent selected form a group consisting of: 1-pentanol, methylal and ethylal; and heating the suspension to obtain a second suspension.

The suspension is provided, preferably by combining DMAc solvate of Fluticasone furoate and the solvent. Then, the said suspension is heated and a second suspension is formed. Preferably, heating is to a temperature of about 42° C. to about 86° C., depending on the solvent. For examples, when 1-pentanol is used, the suspension is heated to a temperature of about 80° C., when methylal is used the suspension is heated to a temperature of about 42° C.; and when ethylal is used it is heated to a temperature of about 86° C.

Preferably, heating is done over a period of about 1 hour.

The second suspension can be cooled, prior to performing a recovery process.

Preferably, cooling is to a temperature of about 0° C., preferably over a period of about 1 hour.

The second suspension can then be further maintained. Preferably, marinating is done upon stirring, preferably for a period of about 2 hours.

The recovery process may comprise, for example, filtering the said crystalling form and drying. Preferably drying is done under nitrogen. Preferably, drying is done at a temperature of about 25° C. to about 35° C., preferably for a period of about 60 minutes to about 120 minutes.

In one embodiment, the present invention encompasses solvates of Fluticasone furoate selected from a group consisting of: tert-Butanol, 1,3 Dimethyl-3,4,5,6-tetrahydro-2(1H)-pyrimidinone ("DMPU") and 1,3 dimethylimidazolidinone ("DMI").

The crystalline forms of Fluticasone furoate, as described in any of the embodiments or combination of embodiments disclosed herein, can be used to prepare pharmaceutical compositions.

The present invention further encompasses 1) a pharmaceutical composition comprising any one, or combination, of crystalline Forms of Fluticasone furoate described in any embodiments or combination of embodiments above and at least one pharmaceutically acceptable excipient and 2) the use of any one, or combination, of the above-described crystalline Forms of Fluticasone furoate, in the manufacture of a pharmaceutical composition, wherein the pharmaceutical composition can be useful for the treatment of asthma, allergic rhinitis, eczema and psoriasis.

The pharmaceutical composition of the present invention can be in a solid or a non-solid form. If the pharmaceutical composition is in a non-solid form, any one, or combination of the crystalline Forms of Fluticasone furoate, within the composition, are retained as solid(s) in the non-solid pharmaceutical composition, e.g., as a suspension, foam, ointment and etc.

The pharmaceutical composition can be prepared by a process comprising combining any one, or combination, of the above-described crystalline Forms of Fluticasone furoate with at least one pharmaceutically acceptable excipient. The crystalline Forms of Fluticasone furoate can be obtained by any of the processes of the present invention as described above.

The pharmaceutical composition can be used to make appropriate dosage forms such as tablets, powders, capsules, suppositories, sachets, troches and losenges.

Any one, or combination, of the above-described crystalline Forms of Fluticasone furoate of the present invention, particularly in a pharmaceutical composition and dosage form, can be used to treat asthma, allergic rhinitis, eczema and psoriasis in a mammal such as a human, comprising administering a treatment effective amount of the one, or combination, of the crystalline Forms of Fluticasone furoate in the mammal. The treatment effective amount or proper dosage to be used can be determined by one of ordinary skill in the art, which can depend on the method of administration, the bioavailability, the age, sex, symptoms and health condition of the patient, and the severity of the disease to be treated, etc.

EXAMPLES

XRD

The XRPD peaks referred to throughout and in the examples below, were obtained using an ARL X-ray powder diffractometer model X'TRA-030, Peltier detector, round standard aluminum sample holder with round zero background quartz plate was used. The cathode is CuKα radiation, λ=1.5418 Å. Scanning parameters: Range: 2-40 deg. 2 θ, continuous Scan, Rate: 3 deg./min. The accuracy of peak positions is defined as +/−0.2 degrees due to experimental differences like instrumentations and sample preparations.

FT-IR Spectroscopy

Perkin-Elmer Spectrum 1000 Spectrometer, at 4 cm$^{-1}$ resolution with 16 scans, in the range of 4000-400 cm$^{-1}$. Samples were analysed in Nujol mull. The spectra were recorded using an empty cell as a background Perkin-Elmer Spectrum One Spectrometer, at 4 cm$^{-1}$ resolution with 16 scans, in the range of 4000-400 cm$^{-1}$. Samples were analysed in KBr with Drift technique. The spectra were recorded using KBr as a background.

Thermal Gravimetric Analysis (TGA)

TGA/SDTA 851$^e$, Mettler Toledo, Sample weight 7-15 mg.
Heating rate: 10° C./min., In N$_2$ stream: flow rate=50 ml/min
Scan range: 30-250° C.

Example 1

Procedure for the Preparation of Fluticasone Furoate Form 4

Fluticasone furoate DMAc solvate (70 mg) were suspended in 1-pentanol (2 ml) at room temperature. The suspension was cooled to 0° C. through 10 minutes and was stirred for 10 minutes at 0° C. Then, it was heated to 80° C. through 60 minutes and was stirred for 10 minutes at 80° C. Then, it was cooled to 0° C. through 60 minutes and was stirred for 120 minutes at 0° C. The suspension was then filtrated and dried 60 minutes at 35° C. under N$_2$.
35 mg of Fluticasone furoate form 4 were obtained.
TGA result: up to 0.3%, PXRD: FIG. 1.

Example 2

Procedure for the Preparation of Fluticasone Furoate Form 4

Fluticasone furoate DMAc solvate (70 mg) were suspended in isobutylacetate (2 ml) at room temperature. The suspension was cooled to 0° C. through 10 minutes and was stirred for 10 minutes at 0° C. Then, it was heated to 98° C. through 60 minutes and was stirred for 10 minutes at 98° C. Then, it was cooled to 0° C. through 60 minutes and was stirred for 120 minutes at 0° C. The suspension was then filtrated and dried 60 minutes at 35° C. under N$_2$.
20 mg of Fluticasone furoate form 4 were obtained.
TGA result: up to 0.3%, PXRD: FIG. 1.

Example 3

Procedure for the Preparation of Fluticasone Furoate Form 4

Fluticasone furoate DMAc solvate (90 mg) were suspended in methylal (3 ml) at room temperature. The suspension was cooled to 0° C. through 10 minutes and was stirred for 10 minutes at 0° C. Then, it was heated to 42° C. through 60 minutes and was stirred for 10 minutes at 42° C. Then, it was cooled to 0° C. through 60 minutes and was stirred for 120 minutes at 0° C. The suspension was then filtrated and dried 60 minutes at 35° C. under N$_2$.
40 mg of Fluticasone furoate form 4 were obtained.
TGA result: up to 0.3%, PXRD: FIG. 1.

Example 4

Procedure for the Preparation of Fluticasone Furoate Form 4

Fluticasone furoate DMAc solvate (95 mg) were suspended in ethylal (3 ml) at room temperature. The suspension was cooled to 0° C. through 10 minutes and was stirred for 10 minutes at 0° C. Then it was heated to 86° C. through 60 minutes and was stirred for 10 minutes at 86° C. Then, it was cooled to 0° C. through 60 minutes and was stirred for 120 minutes at 0° C. The suspension was then filtrated and dried 60 minutes at 35° C. under N2.
92 mg of Fluticasone furoate form 4 were obtained.
TGA result: up to 0.3%, PXRD: FIG. 1.

Example 5

Procedure for the Preparation of Fluticasone Furoate Form 4

Fluticasone furoate DMAc solvate (100 mg) were suspended in propylal (3 ml) at room temperature. The suspension was cooled to 0° C. through 10 minutes and was stirred for 10 minutes at 0° C. Then it was heated to 80° C. through 60 minutes and was stirred for 10 minutes at 80° C. Then, it was cooled to 0° C. through 60 minutes and was stirred for 1'20 minutes at 0° C. The suspension was then filtrated and dried 60 minutes at 35° C. under N$_2$.
93 mg of Fluticasone furoate form 4 were obtained.
TGA result: up to 0.3%, PXRD: FIG. 1.

Example 6

Procedure for the Preparation of Fluticasone Furoate Form A

Fluticasone furoate was purified (by ethylacetate/H$_2$O) and the mother liquors were concentrated to residual volume, to obtain an oily residue. Then, 80 mL of THF were added.
The mixture was stirred to reflux until solution formation and cooled to 20° C. Then, the suspension was stirred at temperature of about room temperature, for about 2 hours. The suspension was filtered off, washed with THF and dried at about room temperature. 12 g of Fluticasone furoate were obtained.
TGA:13.1%, it is Fluticasone furoate form A PXRD; FIG. 3

Example 7

Procedure for the Preparation of Fluticasone Furoate Form A

Fluticasone furoate (1.0 g) was dried at 100° C. under vacuum for 24 h. 0.99 g of Fluticasone furoate were obtained (no desolvatation occurred).

TGA: 12.7%, GC: 13.2% THF; it is Fluticasone furoate form A, PXRD: FIG. 4.

Example 8

Procedure for the Preparation of Fluticasone Furoate Form D

Fluticasone furoate DMA solvate (5.0 g) were suspended in tert-butanol (100 mL). The suspension was stirred at 60° C. for 1 h., then cooled to room temperature, filtered, washed with tert-butanol and dried at 50° C. for 16 h. Fluticasone furoate (4.40 g) were obtained. TGA: 12.1%, It is Fluticasone furoate form D, PXRD: FIG. 7

Example 9

Procedure for the Preparation of Fluticasone Furoate Form F 0.8 grams Fluticasone furoate DMF solvate was dissolved at 2.4 ml of 1,3 dimethylimidazolidinone (DMI) at 80° C. The solution was cooled to the R.T. and 12 ml of water was added. White suspension is stirred for 60 minutes at R.T. The crystals are then isolated by filtration, washed by water, dried for 2 hours at 35° C. under nitrogen to get white solids. (wet sample). TGA result: 21.8%, PXRD: FIG. 9.

Example 10

Procedure for the Preparation of Fluticasone Furoate Form F

A mixture of 0.5 g Fluticasone furoate DMAc solvate and 1.5 ml of DMI were dissolved at 25° C., heated to 50° C. and 4.2 ml of water was added dropwise to the creation of white suspension, stirring at 50° C. for 2.5 hours and than white crystals were isolated and washed with water to get the titled compound.

TGA result: 17.3%, PXRD: FIG. 10.

Example 11

Procedure for the Preparation of Fluticasone Furoate Form F 5.8 grams of 6α,9α-Difluoro-17α-(2-furanylcarbonyl)oxy)-11β-hydroxy-16α-methyl-3-oxo-androsta-1,4-diene-17β-carbothionic acid, a Fluticasone furoate intermediate 1 and imidazole (0.9 g) were suspended in 60 ml of DMI, bromofluoromethane (2.4 g as 54% solution in DMI) were added and the suspension stirred at 40° C. for 15 min., then cooled at 30° C. for 30 min. and then kept at 20° C. for 2 h: at 30° C. a solution was obtained. After reaction completion (judged by HPLC analysis), the mixture was warmed at 35° C. and 120 ml of water were slowly added during 1 hour, resulting in a suspension formation that was then cooled at 0° C. for 2 hours. The solid was filtered off, washed with water and dried at 60° C. under vacuum for 16 hours. Fluticasone furoate DMI solvate (6.10 g) was obtained.

TGA result: 15.9%, PXRD: FIG. 10

Example 12

Procedure for the Preparation of Fluticasone Furoate Form G 0.5 gram Fluticasone furoate unsolvated form 1 was dissolved at 30° C. in 1 ml DMPU.
After 1-2 minutes 5 ml of water was added to the solution, white precipitation was formed. The white suspension was stirred for 1 hour at room temperature. The crystals were then isolated by filtration, washed by water and dried for 2 hours at 35° C. under nitrogen to get white solids TGA result: 20.2%, PXRD: FIG. 12.

Example 13

Procedure for the Preparation of Fluticasone Furoate Form H

Fluticasone DMAc solvate (70 mg) were suspended in 2-butanol (2 ml) at room temperature. The suspension was cooled to 0° C. through 10 minutes and was stirred for 10 minutes at 0° C. Then, it was heated to 97° C. through 60 minutes and was stirred for 10 minutes at 97° C. Then, it was cooled to 0° C. through 60 minutes and was stirred for 120 minutes at 0° C. The suspension was then filtrated and dried 60 minutes at 35° C. under N2. 55 mg of Fluticasone furoate form H were obtained.

TGA result: 11.6%, PXRD: FIG. 14.

Example 14

Procedure for the Preparation of Fluticasone Furoate Form J

Fluticasone furoate DMAc solvate (100 mg) were suspended in dioxolane (3 ml at room temperature. The suspension was cooled to 0° C. through 10 minutes and was stirred for 10 minutes at 0° C. Then it was heated to 44° C. through 45 minutes. The crystal was dissolved, then cooled to 0° C. through 60 minutes and stirred for 120 minutes at 0° C. The suspension was then filtrated and dried 60 minutes at 35° C. under N2.

65 of Fluticasone furoate form J were obtained.
TGA result: 12.2%, PXRD: FIG. 16.

Example 15

Procedure for the Preparation of Fluticasone Furoate Form K

Fluticasone furoate DMAc solvate (3.6 mg) were dissolved in DMPU (9.1 ml at room temperature. The solution was heated to 50° C. and water was dropped (45.5 ml), the suspension was stirred at 49-50° C. for 2.5 hours. The suspension was then filtrated and dried 60 minutes at 35° C. under N2.
3.1 of Fluticasone furoate form K were obtained.
TGA result: 18.3%, PXRD: 18.

Example 16

Procedure for the Preparation of Fluticasone Furoate Form B

Anhydrous Fluticasone furoate unsolvated (3.0 g) were suspended in Dioxane (100 mL) and water (5 mL) and heated to solution at 60° C. The mixture was diluted with water (95 mL) dropwise. The suspension was cooled to room temperature, filtered off, washed with water and dried at room temperature to give of Fluticasone furoate solvate (3.2 g).

TGA: 14.7% It is Fluticasone furoate form B, PXRD: FIG. 20

Example 17

Procedure for the Preparation of 1-butanol Solvate of Fluticasone Furoate Form C Fluticasone furoate DMA solvate (5.0 g) was suspended in 1-Butanol (100 mL). The suspension was stirred for 24 h. at room temperature, then filtered off, washed with 1-butanol and dried at 50° C. for 16 h. under vacuum. 4.40 g of Fluticasone furoate solvate were obtained.

TGA: 12.1%, Is 1-butanol solvate, form C PXRD: FIG. 22

Example 18

Procedure for the Preparation of Fluticasone Furoate Form E 5.00 grams of 6α,9α-Difluoro-17α-(2-furanylcarbonyl)oxy)-11β-hydroxy-16α-methyl-3-oxo-androsta-1,4-diene-17β-carbothionic acid, a Fluticasone furoate intermediate 1, Pyridine (50 mL) and bromofluoromethane (1.13 g) 9% in Dimethylacetamide were stirred at room temperature for 4 h. The suspension was diluted dropwise with water (60 mL), filtered off, washed with water and dried at R.T, to constant weight. Fluticasone furoate (5.70 g) was obtained.

TGA: 13.4%, it is Fluticasone furoate form E, PXRD: FIG. 23

Example 19

Procedure for the Preparation of Fluticasone Furoate Form 5

2.5 g of Flu.f. b.030309 (DMAc solvate) were suspended to 62.5 ml of 1 pentanol, suspension was heated to 80° C. during 60 min, 10 min. stirred at 80° C., during 60 min cooled to 0° C., 2 h. stirred at 0° C. Filtration, drying 2 hours under N2 at 35° C.

1.8 g was obtained.

Example 20

Procedure for the Preparation of Fluticasone Furoate Form 5

3.0 g of Fluticasone furoate. (DMAc solvate) were suspended to 60.0 ml of methylal, suspension was heated to 42° C. during 60 min, 10 min. stirred at 42° C., during 60 min cooled to 0° C., 2 h. stirred at 0° C. Filtration, drying 60 min. under N2 at 25° C.

1.65 g was obtained.

Example 21

Procedure for the Preparation of Fluticasone Furoate Form 5

3.0 g of Fluticasone furoate (DMAc solvate) were suspended to 60.0 ml of ethylal, suspension was heated to 86° C. during 60 min, 10 min. stirred at 86° C., during 60 min cooled to 0° C., 2 h. stirred at 0° C. Filtration, drying 60 minutes under N2 at 25° C.

2.3 g was obtained.

Example 22

Procedure for the Preparation of Fluticasone Furoate Dimethylformamide ("DMF") Solvate According to U.S. Pat. No. 6,777,399 Example 5

A mixture of 6.alpha.,9.alpha.-Difluoro-17.alpha.-[(2-furanylcarbonyl)oxy]-11.beta.-hydroxy-16.alpha.-methyl-3-oxo-androsta-1,4-diene-17.beta.-carbothioic Acid (4.5 g, 8.88 mmol) in dimethylformamide (DMF) (31 ml) is treated with potassium bicarbonate (0.89 g, 8.88 mmol) and the mixture is cooled to −20° C. A solution of bromofluoromethane (0.95 g, 8.50 mmol, 0.98 eqv.) in dimethylformamide (DMF) (4.8 ml) at 0° C. is added and the mixture is stirred at −20° C. for 4 hours. The mixture is then stirred at −20° C. for a further 30 minutes, added to 2M hydrochloric acid (100 ml) and stirred for a further 30 minutes at 0-5° C. The precipitate collected by vacuum filtration, washed with water and dried at 50° C. to give the title compound (4.47 g, 82%). NMR .delta.((CD$_3$OD) includes the peaks described for 6.alpha.,9.alpha.-Difluoro-17.alpha.-[(2-furanylcarbonyl)oxy]-11.beta.-hydroxy-16.alpha.-methyl-3-oxo-androsta-1,4-diene-17.beta.-carbothioic Acid S-fluoromethyl Ester and the following additional solvent peaks: 7.98 (1H, bs), 2.99 (3H, s), 2.86 (3H, s).

Example 23

Procedure for the Preparation of Fluticasone Furoate Dimethylacetamide ("DMAc") Solvate According to U.S. Pat. No. 6,777,399 Example 15

6.alpha.,9.alpha.-Difluoro-17.alpha.-[(2-furanylcarbonyl)oxy]-11.beta.-hydroxy-16.alpha.-methyl-3-oxo-androsta-1,4-diene-17.beta.-carbothioic Acid S-fluoromethyl Ester (100 mg) was dissolved in dimethylacetamide (0.5 mL) at approximately 20° C. and left to slowly crystallize over a period of 6 days. The solid was recovered by filtration and then dried under vacuum at approximately 60° C. for 16 hours to afford the title compound.

Stoichiometry of compound of formula (I): guest=1:1 from .sup.1 H NMR (CDCl$_3$)

We claim:

1. A Fluticasone furoate solvate selected from a group consisting of tert-Butanol, 2-butanol, dioxalane, 1,3 Dimethyl-3,4,5,6-tetrahydro-2(1H)-pyrimidinone ("DMPU") and 1,3 dimethylimidazolidinone ("DMI").

2. The Fluticasone furoate solvate according to claim 1, wherein the solvate is crystalline.

3. The crystalline Fluticasone furoate solvate according to claim 2, wherein the solvate is tert-butanol.

4. The crystalline Fluticasone furoate tert-butanol solvate according to claim 3, characterized by data selected from: a powder XRD pattern having peaks at about 9.0, 10.6, and 14.3±0.2 degrees two-theta, and further having any 2 powder XRD peaks selected from the list: 14.8, 15.9, 17.8, 18.1, 18.6, 18.8 and 21.2±0.2 degrees 2-theta; a powder XRD pattern having peaks at about 9.0, 10.6, 14.3, 14.8 and 15.9±0.2 degrees two-theta; a powder XRD pattern as depicted in FIG. 7; and any combination thereof.

5. The crystalline Fluticasone furoate solvate according to claim 2, wherein the solvate is 2-butanol.

6. The crystalline Fluticasone furoate 2-butanol solvate according to claim 5, characterized by data selected from: a powder XRD pattern having peaks at about 8.1, 9.6, 13.7, 14.6 and 15.2±0.2 degrees two-theta; a powder XRD pattern as depicted in FIG. 14; and any combination thereof.

7. The crystalline Fluticasone furoate solvate according to claim 2, wherein the solvate is dioxolane.

8. The crystalline Fluticasone furoate dioxolane solvate according to claim 7, characterized by data selected from: a powder XRD pattern having peaks at about 9.9, 14.1, 15.1, 15.7 and 19.8±0.2 degrees two-theta; a powder XRD pattern as depicted in FIG. 16; and any combination thereof.

9. The crystalline Fluticasone furoate solvate according to claim 2, wherein the solvate is 1,3 dimethyl-3,4,5,6-tetrahydro-2(1H)-pyrimidinone ("DMPU").

10. The crystalline Fluticasone furoate DMPU solvate according to claim 9, characterized by data selected from: powder XRD pattern having peaks at about 8.6, 13.4, and 22.6±0.2 degrees two-theta, and further having any 2 powder XRD peaks selected from the list: 10.8, 12.7, 14.5, 15.1, 19.0, 21.0 and 23.8±0.2 degrees 2-theta; a powder XRD pattern having peaks at about 8.6, 13.4, 15.1, 19.0 and 22.6±0.2 degrees two-theta; a powder XRD pattern as depicted in FIG. 12; and any combination thereof.

11. The crystalline Fluticasone furoate solvate according to claim 2, wherein the solvate is 1,3 dimethylimidazolidinone ("DMP").

12. The crystalline Fluticasone furoate DMI solvate according to claim 11, characterized by data selected from: a powder XRD pattern having peaks at about 7.4, 12.5, and 17.7±0.2 degrees two-theta, and further having any 2 powder XRD peaks selected from the list: 13.2, 15.3, 18.7, 19.6, 22.3 and 24.0±0.2 degrees 2-theta; a powder XRD pattern having peaks at about 7.4, 12.5, 15.3, 17.7 and 19.6±0.2 degrees two-theta; a powder XRD pattern as depicted in FIG. 9; a powder XRD pattern as depicted in FIG. 10; and any combination thereof.

13. A pharmaceutical composition comprising at least one of the solvates of Fluticasone furoate according to claim 1, and at least one pharmaceutically acceptable excipient.

14. A method of treatment of asthma, allergic rhinitis, eczema and psoriasis in mammals, including humans, which method comprises administering a pharmaceutical composition comprising at least one of the solvates of Fluticasone furoate according to claim 1, and at least one pharmaceutically acceptable excipient, to a patient in need for treatment thereof.

* * * * *